US010670527B2

(12) United States Patent
Cao et al.

(10) Patent No.: US 10,670,527 B2
(45) Date of Patent: Jun. 2, 2020

(54) BIOSENSOR

(71) Applicant: Shenzhen Genorivision Technology Co., Ltd., Shenzhen (CN)

(72) Inventors: Peiyan Cao, Shenzhen (CN); Yurun Liu, Shenzhen (CN)

(73) Assignee: Shenzhen Genorivision Technology Co., Ltd., Shenzhen (CN)

( * ) Notice: Subject to any disclaimer, the term of this patent is extended or adjusted under 35 U.S.C. 154(b) by 0 days.

(21) Appl. No.: 15/309,303

(22) PCT Filed: Sep. 14, 2015

(86) PCT No.: PCT/CN2015/089549
§ 371 (c)(1),
(2) Date: Nov. 7, 2016

(87) PCT Pub. No.: WO2017/045107
PCT Pub. Date: Mar. 23, 2017

(65) Prior Publication Data
US 2018/0180547 A1 Jun. 28, 2018

(51) Int. Cl.
G01N 21/00 (2006.01)
G01N 21/64 (2006.01)
C12Q 1/6825 (2018.01)

(52) U.S. Cl.
CPC ....... *G01N 21/6454* (2013.01); *C12Q 1/6825* (2013.01); *G01N 21/6428* (2013.01);
(Continued)

(58) Field of Classification Search
CPC ............ G01N 21/6486; G01N 21/6428; B01L 2300/0654
(Continued)

(56) References Cited

U.S. PATENT DOCUMENTS 3,787,745 A 1/1974 Wulms
5,773,829 A * 6/1998 Iwanczyk ............. G01T 1/1644
250/367

(Continued)

FOREIGN PATENT DOCUMENTS

CN 101848757 A 9/2010
CN 103223357 A 7/2013
(Continued)

Primary Examiner — Natalia Levkovich
(74) Attorney, Agent, or Firm — IPro, PLLC; Qian Gu

(57) ABSTRACT

Disclosed herein is an apparatus comprising: a probe carrier comprising: a substrate comprising with holes through a thickness of the substrate and a transparent window across an opening of each of the holes, wherein the transparent window closes the opening, wherein one or more locations on the transparent window are configured to have probes attached thereto, wherein interaction between the probes and an analyte generates a signal; an optical system comprising a plurality of collimators; a sensor configured to detect the signal; wherein the collimators can essentially prevent light from passing if a deviation of a propagation direction of the light from an optical axis of the collimators is greater than a threshold. Because the probe carrier is separate and independent from the microarray, the probe carrier may be assembled with a pre-existing microarray prior to its use, and be detached from the microarray and disposed after its use.

22 Claims, 30 Drawing Sheets

(52) U.S. Cl.
 CPC ............... *B01J 2219/00603* (2013.01); *B01J 2219/00702* (2013.01); *G01N 2021/6471* (2013.01)

(58) Field of Classification Search
 USPC .................. 422/82.05, 82.09, 82.08, 552
 See application file for complete search history.

(56) References Cited

U.S. PATENT DOCUMENTS

| | | |
|---|---|---|
| 6,287,871 B1 | 9/2001 | Herron et al. |
| 6,297,489 B1 | 10/2001 | Suyama et al. |
| 2005/0074784 A1 | 4/2005 | Vo-Dinh |
| 2008/0265769 A1 | 10/2008 | Contarino et al. |
| 2009/0315443 A1 | 12/2009 | Sullivan et al. |
| 2010/0140460 A1 | 6/2010 | Rigneault et al. |
| 2011/0053799 A1 | 3/2011 | Abiko et al. |
| 2012/0170114 A1 | 7/2012 | Domash et al. |
| 2014/0001341 A1 | 1/2014 | Hassibi et al. |
| 2014/0256057 A1 | 9/2014 | Ozawa et al. |
| 2014/0274746 A1 | 9/2014 | Khurana et al. |
| 2014/0295577 A1 | 10/2014 | Matsuzawa et al. |
| 2015/0079596 A1 | 3/2015 | Eltoukhy et al. |

FOREIGN PATENT DOCUMENTS

| | | |
|---|---|---|
| CN | 103296035 A | 9/2013 |
| CN | 103857997 A | 6/2014 |
| DE | 102008011793 A1 | 9/2009 |
| DE | 102012018303 A1 | 3/2014 |
| WO | 0103833 A1 | 1/2001 |
| WO | 2015089092 A1 | 6/2015 |

\* cited by examiner

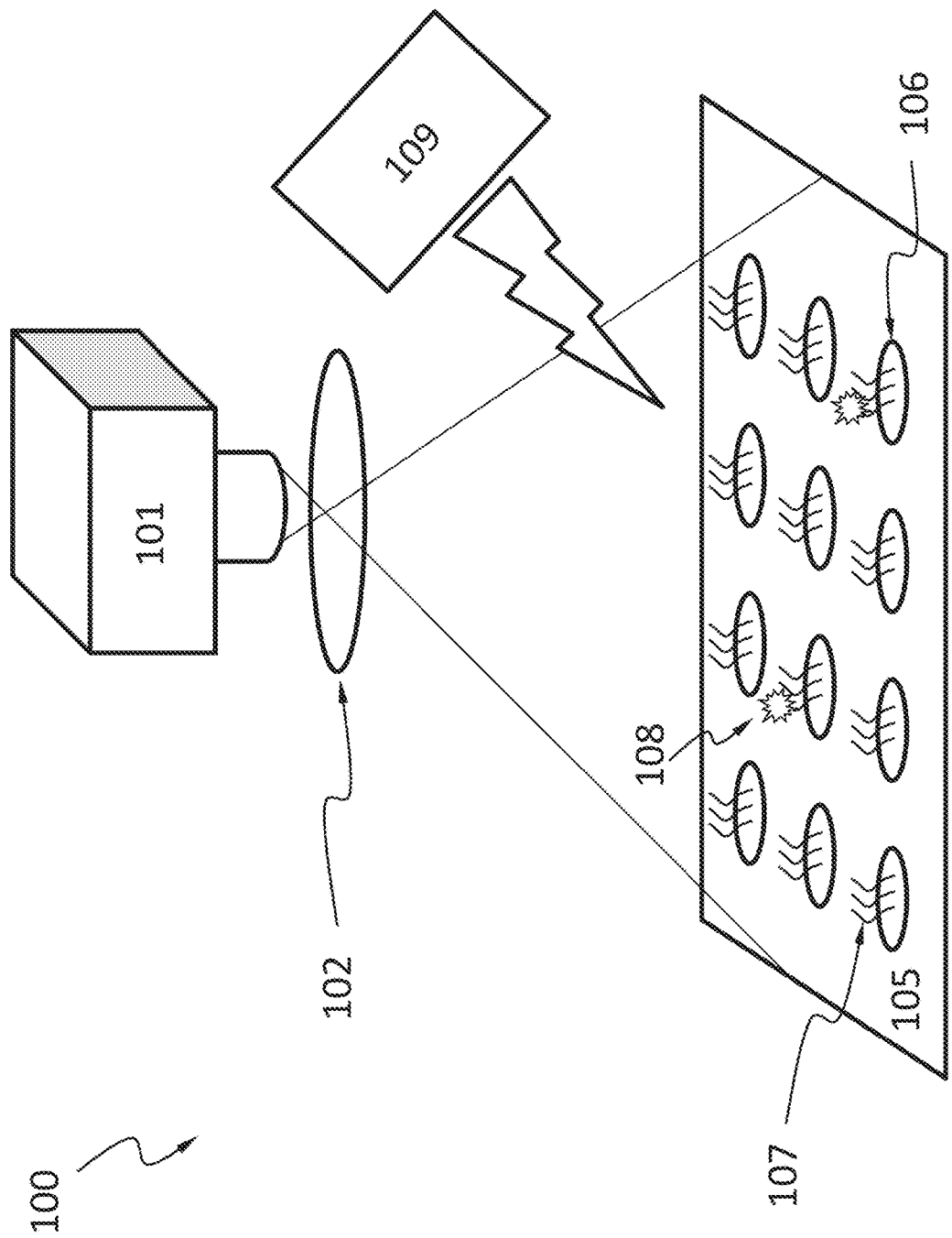

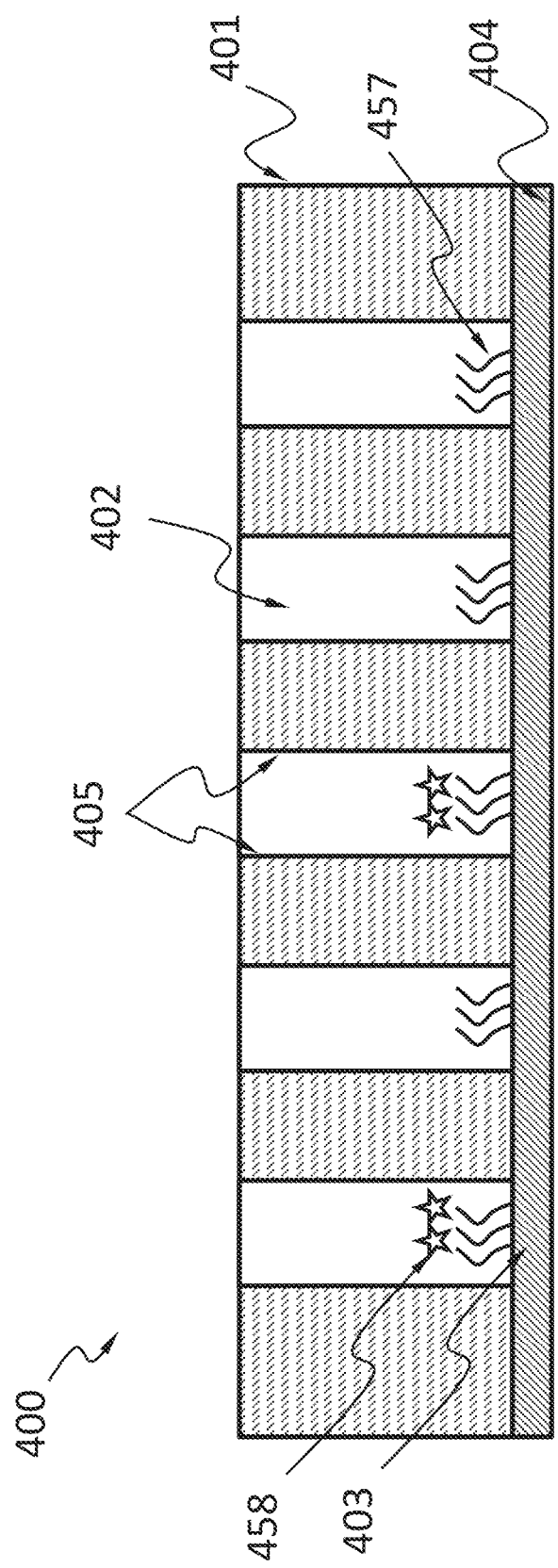

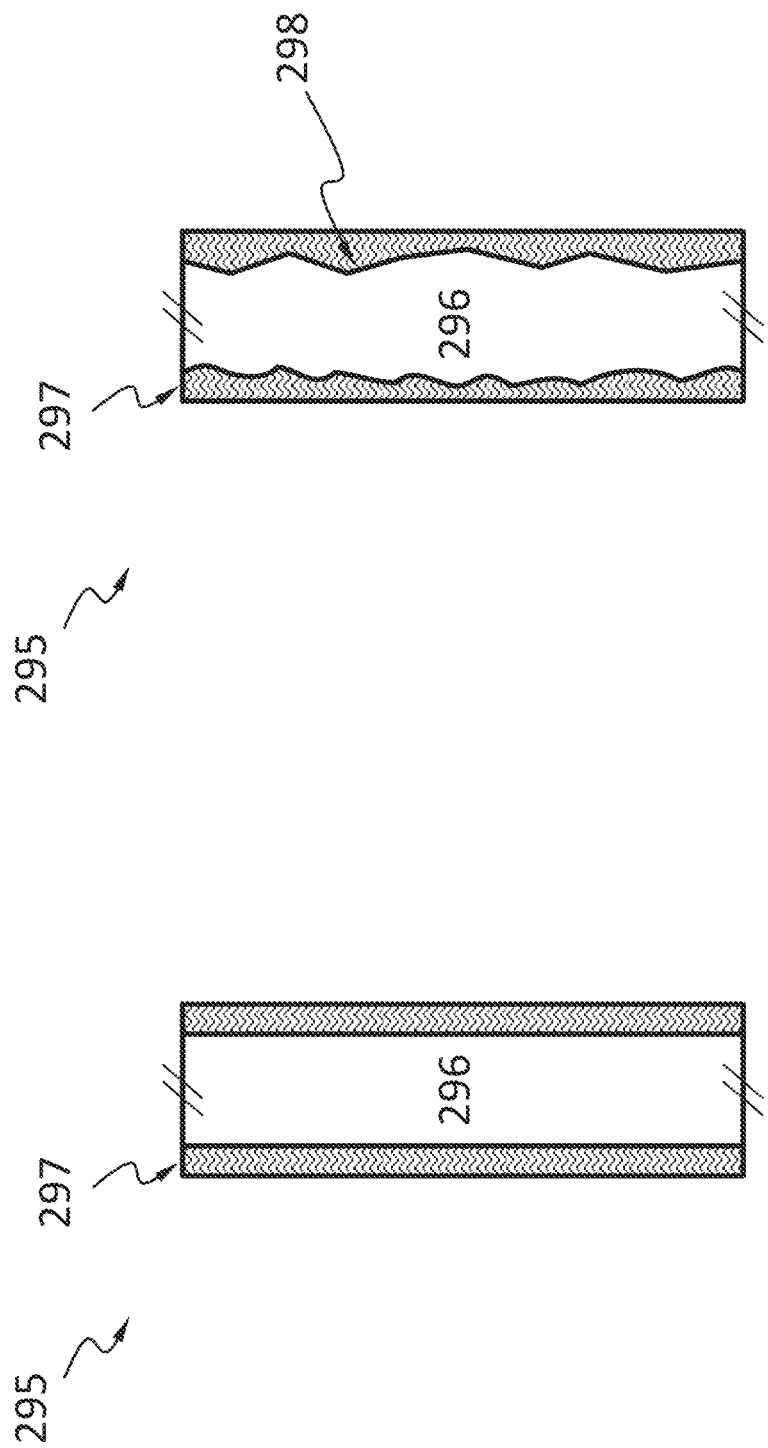

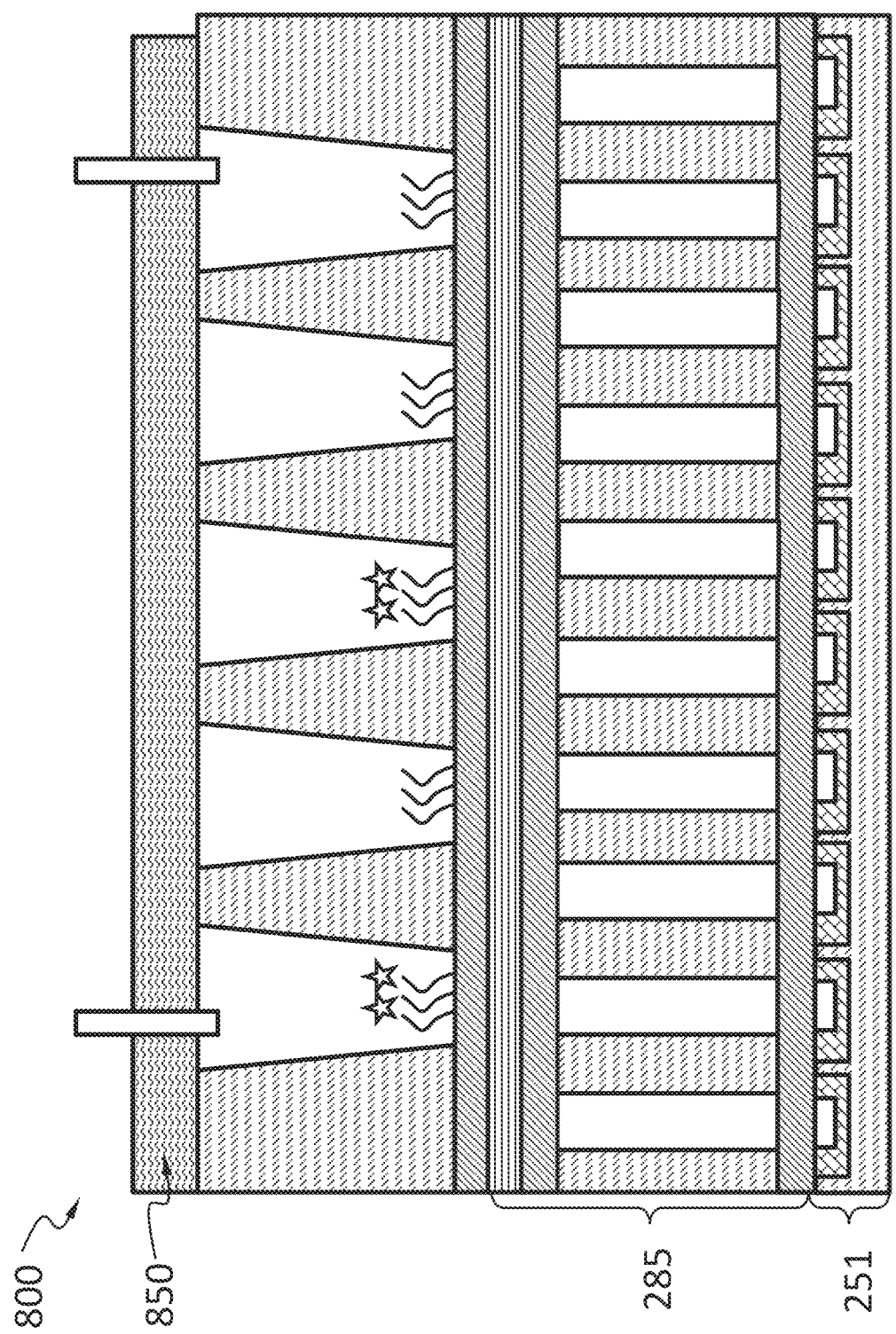

BIOSENSOR

TECHNICAL FIELD

The disclosure herein relates to biosensors, particularly biosensors based on optical detection.

BACKGROUND

A biosensor is an analytical device for detection of an analyte involved in a biological process. For example, the analyte may be a DNA, a protein, a metabolite, or even a living organism (e.g., bacteria, virus).

A biosensor usually has a probe that interacts with the analyte. The probe may be designed to bind or recognize the analyte. Examples of the probe may include antibodies, aptamers, DNAs, RNAs, antigens, etc. Interaction between the probe and the analyte may lead to one or more detectable event. For example, the detectable event may be release of a chemical species or a particle (e.g., a quantum dot), a chemical reaction, luminescence (e.g., chemiluminescence, bioluminescence, electrochemiluminescence, electroluminescence, photoluminescence, fluorescence, phosphorescence), change in a physical property (e.g., Raman scattering, color) or chemical property (e.g., reactivity, reaction rate).

A biosensor may have a detector that can detect the detectable event as a result of the interaction. The detector may transform the detectable event into another signal (e.g., image, electrical signal) that can be more easily measured and quantified. The detector may include circuitry that obtains data from the detectable event and processes the data.

One type of biosensor is microarrays. A microarray can be a two-dimensional array on a solid substrate (e.g., a glass slide, a silicon wafer). The array may have different assays at different locations. The assays at different locations may be independent controlled or measured, thereby allowing multiplexed and parallel sensing of one or many analytes. A microarray may be useful in miniaturizing diagnosis assays. For example, a microarray may be used for detecting biological samples in the fields without sophisticated equipment, or be used by a patient who is not in a clinic or hospital to monitor his or her physiological symptoms.

SUMMARY

Disclosed herein is an apparatus comprising: a probe carrier comprising: a substrate comprising a plurality of holes through a thickness of the substrate and a transparent window across an opening of each of the holes, wherein the transparent window closes the opening, wherein one or more locations on the transparent window are configured to have probes attached thereto, wherein interaction between the probes and an analyte generates a signal; an optical system comprising a plurality of collimators; a sensor comprising a plurality of pixels configured to detect the signal; wherein the collimators are configured to essentially prevent light from passing if a deviation of a propagation direction of the light from an optical axis of the collimators is greater than a threshold.

According to an embodiment, the substrate comprises silicon.

According to an embodiment, the probes and the substrate are on a same side of the probe carrier.

According to an embodiment, the probes and the substrate are on opposite sides of the probe carrier.

According to an embodiment, the transparent window is aligned with one of the collimators.

According to an embodiment, the transparent window encompasses more than one of the collimators.

According to an embodiment, the transparent window is a portion of a continuous transparent layer across the substrate.

According to an embodiment, the transparent window has a thickness from 10 to 50 micrometers.

According to an embodiment, the sidewall of the hole is not perpendicular to the transparent window.

According to an embodiment, the sensor comprises a control circuit configured to control, acquire data from, or process data from the pixels.

According to an embodiment, the pixels are arranged such that each of the pixels is optically coupled to one or more of the locations.

According to an embodiment, the pixels are optically coupled to the locations by the collimators.

According to an embodiment, the signal is luminescence.

According to an embodiment, the signal is generated under excitation of an excitation radiation.

According to an embodiment, the optical system further comprises a filter, wherein the filter is configured to block at least a portion of the excitation radiation.

According to an embodiment, the filter is a dichroic filter.

According to an embodiment, the optical system further comprises or a transmissive layer.

According to an embodiment, the optical system further comprises a plurality of microlens.

According to an embodiment, the threshold is 20°.

According to an embodiment, the collimators comprises a meta-material, quantum dots or a photonic crystal.

According to an embodiment, the collimators are configured to eliminate optical cross-talk between neighboring pixels among the plurality of pixels.

According to an embodiment, at least one of the collimators comprises a core and a sidewall surrounding the core.

According to an embodiment, the signal is generated under excitation of an excitation radiation; wherein the core is a material that essentially prevents the excitation radiation from passing through irrespective of propagation direction of the excitation radiation.

According to an embodiment, the signal is generated under excitation of an excitation radiation; wherein the core comprises a dichroic filter.

According to an embodiment, the core allows the signal to pass through essentially unabsorbed.

According to an embodiment, the core is a void space.

According to an embodiment, the sidewall attenuates a portion of the signal reaching the sidewall.

According to an embodiment, the sidewall is textured.

According to an embodiment, the apparatus further comprises a redistribution layer configured to route data from the pixels.

According to an embodiment, the filter comprises a meta-material, quantum dots or a photonic crystal.

BRIEF DESCRIPTION OF FIGURES

FIG. 1A schematically shows an apparatus including a microarray.

FIG. 4A schematically shows a probe carrier 400 wherein the probes and the substrate are on a same side of the probe carrier, according to an embodiment.

FIG. 7C schematically shows a collimator, according to an embodiment.

FIG. 7D schematically shows a collimator, according to an embodiment.

FIG. 8 schematically shows an apparatus 800 in which the optical system may have a microfluidic system, according to an embodiment.

DETAILED DESCRIPTION

Figure 1B:
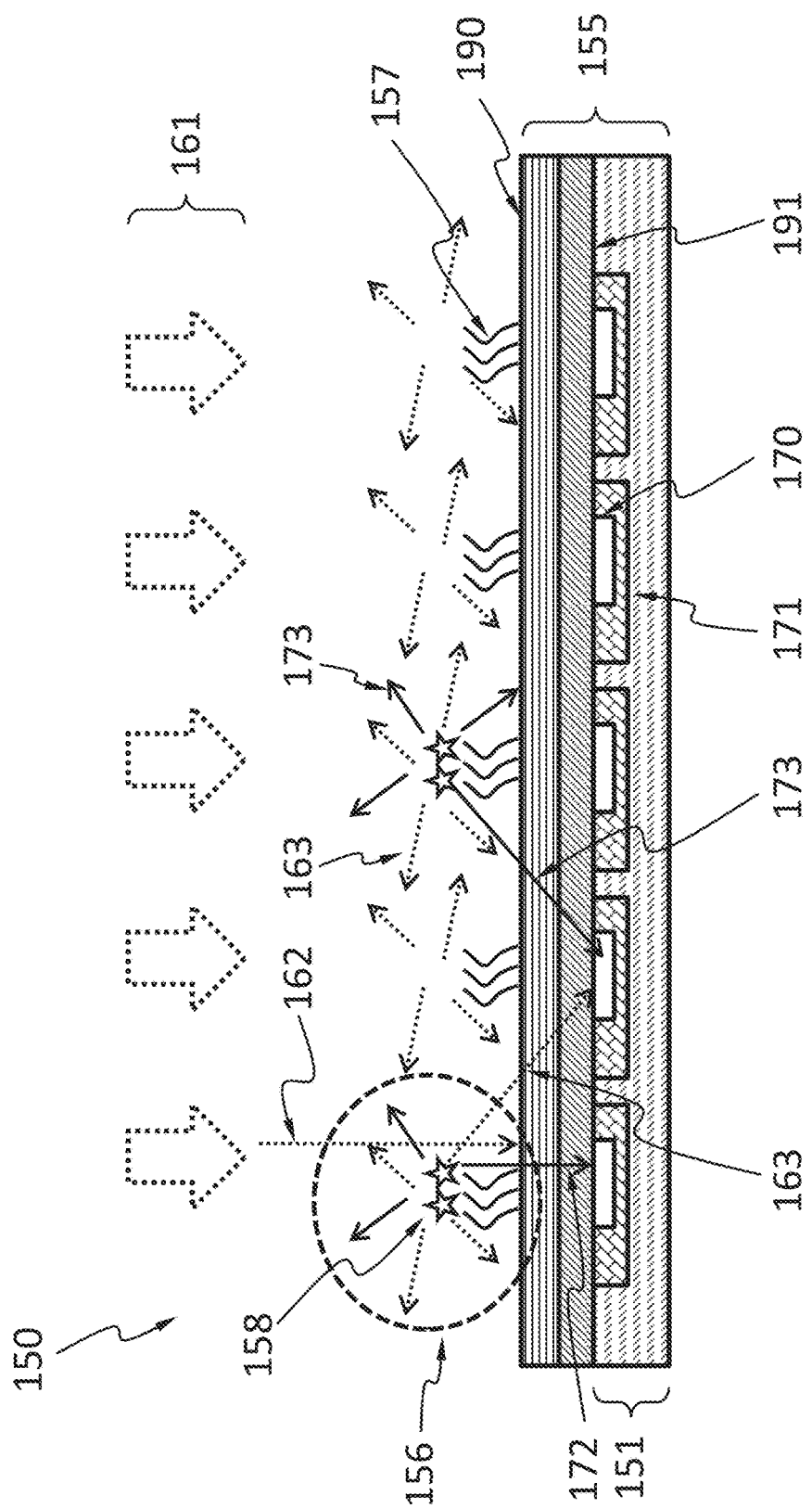
FIG. 1B schematically shows an apparatus where detector capability is integrated into a microarray.

FIG. 1A schematically shows an apparatus 100 including a microarray 105. The system 100 may have an image sensor 101, an optical system 102, and/or an excitation source 109. The image sensor 101 may be configured to measure an optical property (e.g., color, intensity) at different locations 106 of the microarray 105. The locations 106 may have various probes 107 attached thereto. The probes 107 may interact with analyte and the interaction may generate signals 108 detectable by the image sensor 101. The generation of the signals 108 may need excitation by the excitation source 109 (e.g., laser, UV light, etc.). The image sensor 101 and the optical system 102 of the system 100 tend to be bulky, fragile, or expensive and may not have high enough spatial resolution to distinguish one location from its neighboring locations.

FIG. 1B schematically shows a system 150 where detector capability is integrated into a microarray 155. The microarray 155 may have multiple locations 156 with various probes 157 attached thereto. The probes 157 may interact with various analytes and the interaction may generate signals 158 detectable by a sensor 151 integrated to the microarray 155. For example, the analytes are fluorophore-labeled nucleic acid or protein fragments; the probes are oligonucleotides or antibodies. Locations with fluorophore-labeled analytes captured by the probes can be identified by detecting fluorescence from the fluorophores on the captured analytes. The sensor 151 may have multiple pixels 170 configured to detect the signals 158 (e.g., color, intensity). The pixels 170 may have a control circuit 171 configured to control, acquire data from, and/or process data from the pixels 170. The pixels 170 may be arranged such that each pixel 170 is optically coupled to one of the locations 156. However, the signals 158 generated at one location 156 may not entirely reach the pixel 170 optically coupled to that location 156. A portion 172 of the signals 158 may reach the pixel 170 optically coupled to that location 156 but another portion 173 may be scattered into neighboring pixels ("optical cross-talk") and/or away from all pixels 170. Generating the signals 158 may need an excitation radiation 161 (e.g., laser, UV light, etc.). A portion 162 of the excitation radiation 161 may pass through the locations 156 unscattered. A portion 163 of the excitation radiation 161 may be scattered into some of the pixels 170 or away from all pixels 170. The portion 162 may be blocked by a filter 190 from reaching the pixels 170. The filter 190 may be position below or above a transmissive layer 191. However, the filter 190 may be sensitive to incident directions and may not block the portion 163, despite portions 162 and 163 have the same wavelength. If the portion 163 reaches the pixels 170, it can overshadow signals 158.

Figure 2A:
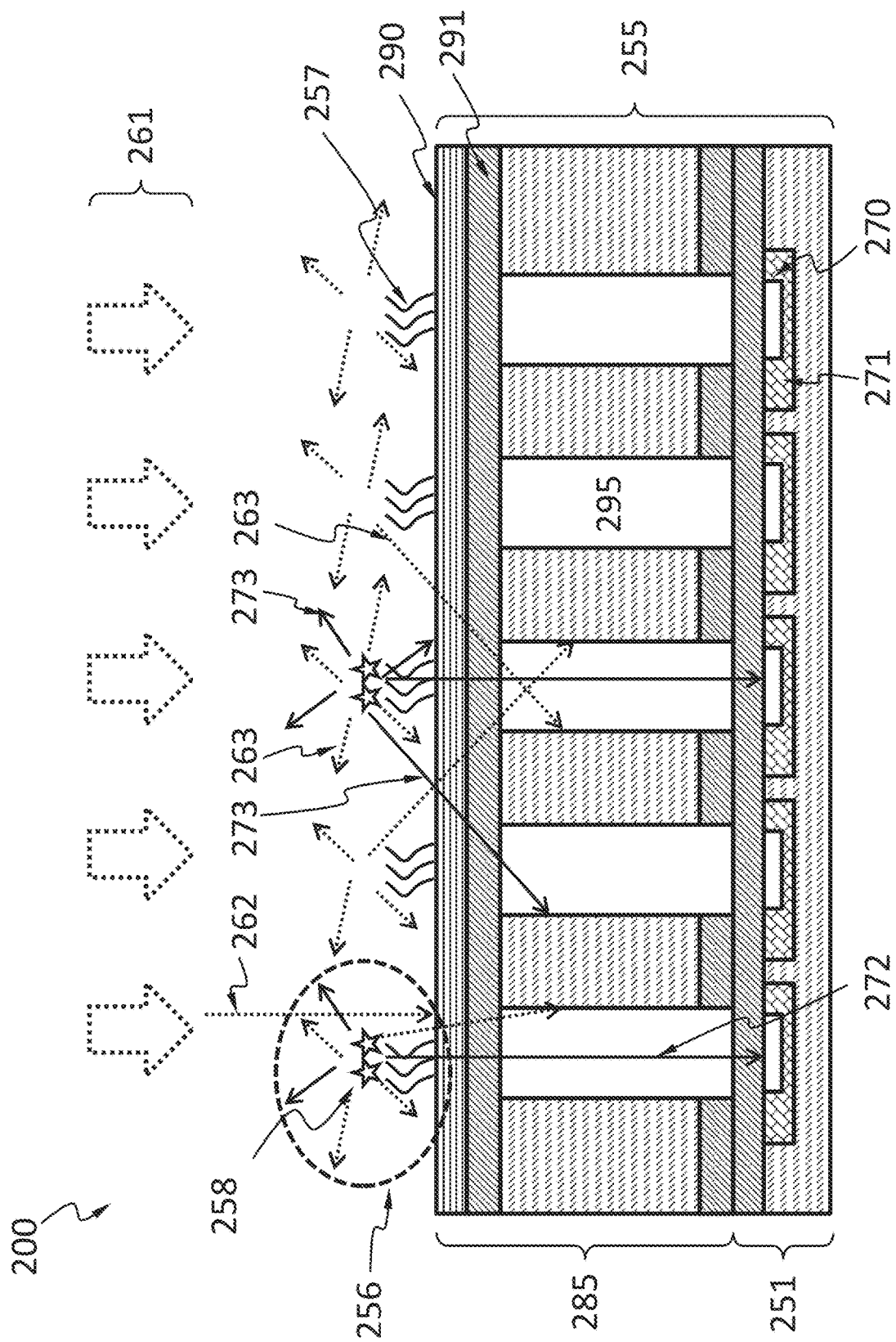
FIG. 2A schematically shows an apparatus, according to an embodiment.
Figure 2B:
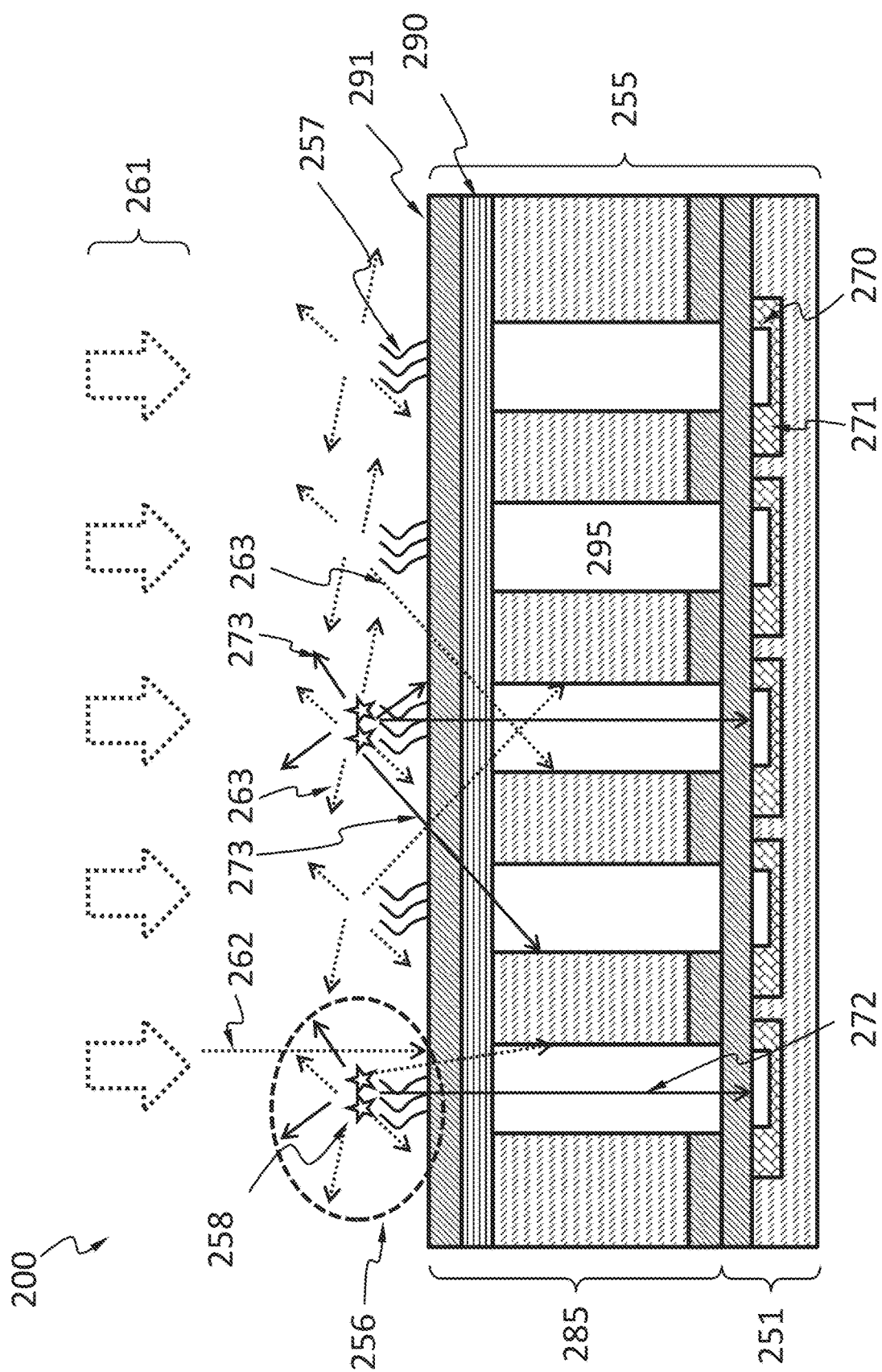
FIG. 2B schematically shows an apparatus, according to an embodiment.

FIG. 2A schematically shows an apparatus 200, according to an embodiment. The system 200 includes a microarray 255 including an integrated sensor 251 and an optical system 285. The microarray 255 may have multiple locations 256 with various probes 257 attached thereto. The probes 257 may interact with various analytes and the interaction may generate signals 258 detectable by the sensor 251. The sensor 251 may have multiple pixels 270 configured to detect the signals 258 (e.g., color, intensity). The pixels 270 may have a control circuit 271 configured to control, acquire data from, and/or process data from the pixels 270. The pixels 270 may be arranged such that each pixel 270 is optically coupled to one or more of the locations 256. The optical system 285 may include a filter 290 positioned below or above a transmissive layer 291 (FIG. 2B shows an example where the filter 290 is below the transmissive layer 291). The optical system 285 may include a plurality of collimators 295 configured to optically couple the pixels 270 to the locations 256. The filter 290 and the transmissive layer 291 may not have to be fabricated on the same substrate as the collimators 295. Instead, the filter 290 and the transmissive layer 291 may be fabricated and bonded to the collimators 295. In an embodiment, the sensor 251 comprises quantum dots.

In an embodiment, the transmissive layer 291 may include oxide or nitride. For example, the transmissive layer 291 may include glass.

In an embodiment, the filter 290 may be a dichroic filter (also known as interference filter). The filter 290 may be a low-pass (passing frequency below a threshold) or bandpass filter. The filter 290 may include a meta-material, quantum dots or a photonic crystal. A meta-material has component materials arranged in repeating patterns, often at microscopic or smaller scales that are smaller than the wavelengths of the light the meta-material is designed to influence. The structure of the repeated patterns and the properties of the component materials may be selected to tailor the properties of the meta-material. For example, the meta-material may provide optical transparency at all frequencies except at the selected frequency or frequencies which it is configured to block (for example particular laser frequencies that could cause harm to a user). A photonic crystal is a periodic dielectric structure that has a band gap that forbids propagation of a certain frequency range of light. The filter 290 may have multiple thin layers of materials with different refractive indices and may be made by alternately depositing thin layers of these materials. A quantum dot (OD) is a nanocrystal made of semiconductor materials that is small enough to exhibit quantum mechanical properties. Specifically, its excitons are confined in all three spatial dimensions. Quantum dots of the same material, but with different sizes, can absorb light of different wavelengths due to the quantum confinement effect. The larger the quantum dot, the redder (lower energy) its absorption. Conversely, smaller quantum dots absorb bluer (higher energy) light. The filter 290 may be an absorptive filter but it would have sufficient thickness to be effective.

Figure 3A:
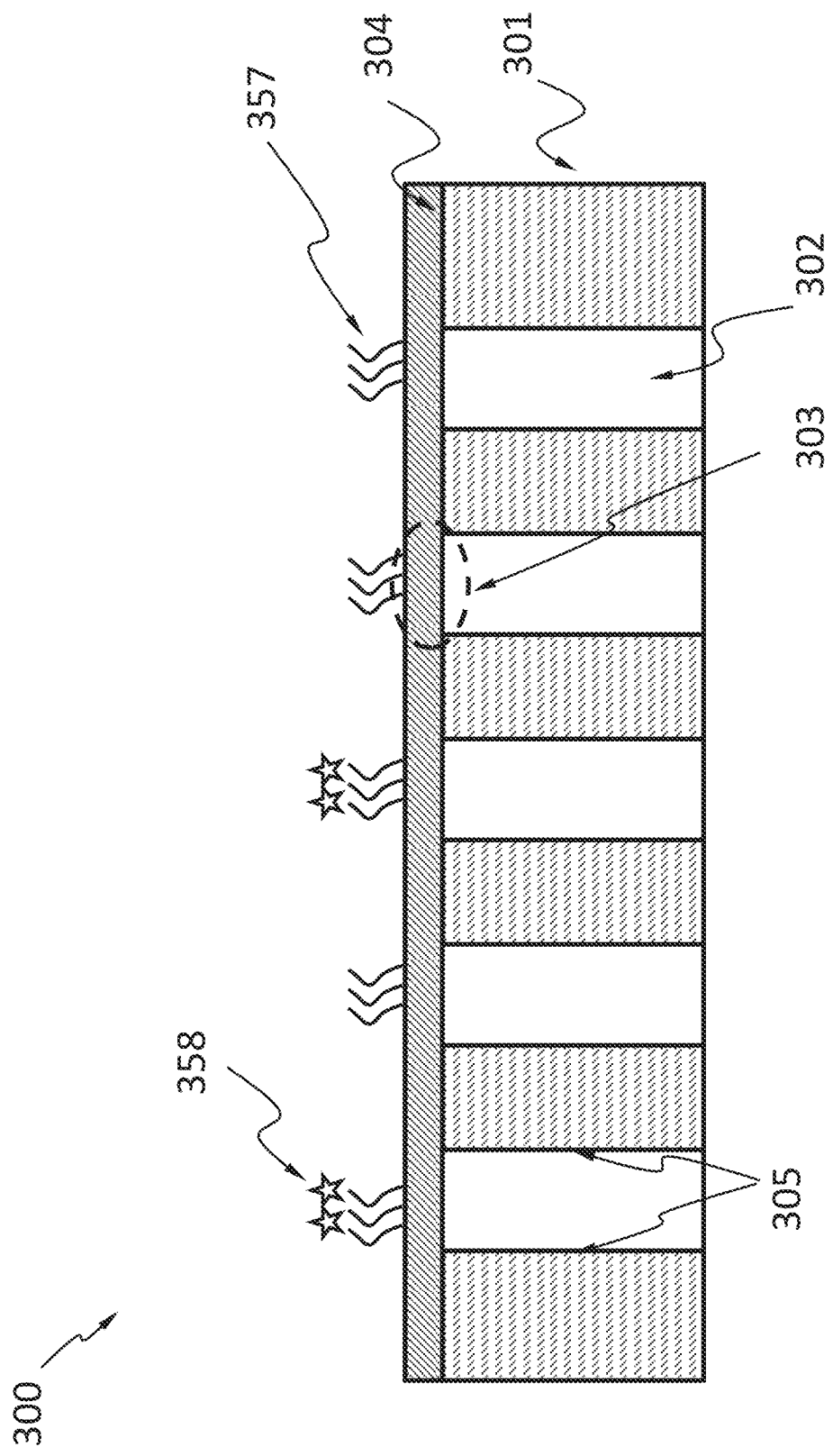
FIG. 3A schematically shows a probe carrier 300 wherein the probes and the substrate are on opposite sides of the probe carrier, according to an embodiment.

FIG. 3A schematically shows a probe carrier 300 wherein the probes and the substrate are on opposite sides of the probe carrier, according to an embodiment. The probe carrier 300 comprises a substrate 301 comprising a plurality of holes 302 through a thickness of the substrate 301 and a transparent window 303 across an opening of each of the holes 302. The transparent window 303 closes the opening, and one or more locations on the transparent window are configured to have probes 357 attached thereto. Interactions between the probes 357 and an analyte generate a signal 358.

According to the embodiment, the probe carrier 300 is separate and independent from the microarray 255 that includes the optical system 285 and integrated sensor 251. Therefore, the probe carrier 300 may be assembled with a microarray prior before its use, and the probe carrier 300 may be detached from the microarray and disposed after its use. Because fabrication of microarray is costly, the probe carrier 300 allows reuse of the microarray 255 including its optical systems and sensors. In addition, the probe carrier 300 allows a user to choose from various microarrays to use with the probe carrier 300, which provides more flexibility and reduces cost in fabrication.

In an embodiment, the substrate 301 comprises silicon or other suitable materials. In an embodiment, the transparent window 303 comprises silicon oxide, silicon nitride or other suitable material. In an embodiment, the transparent window 303 is a portion of a continuous transparent layer 304 across the substrate. In an embodiment, the transparent window 303 or transparent layer 304 has a thickness from 10 to 50 micrometers. The substrate 301 can mechanically support the transparent window 303 or the transparent layer 304.

In an embodiment, the probe carrier is made by the following method: 1) providing a silicon wafer as a substrate; 2) disposing a transparent layer such as a layer of silicon oxide on the substrate; etching the substrate to form holes in the substrate. One of ordinary skill in the art will recognize that wet or dry etching or other suitable techniques may be used to remove portions of the substrate to form the holes of a desired depth. Examples of a dry etching process include, but are not limited to, inductively coupled plasma reactive ion etch (ICP RIE) process, and the Bosch process. Examples of wet etching process include, but are not limited to, a metal assisted chemical etch (MACE) process.

In an embodiment, probes are deposited after forming the holes in the substrate. In another embodiment, probes are deposited before forming the holes in the substrate.

Figure 3B:
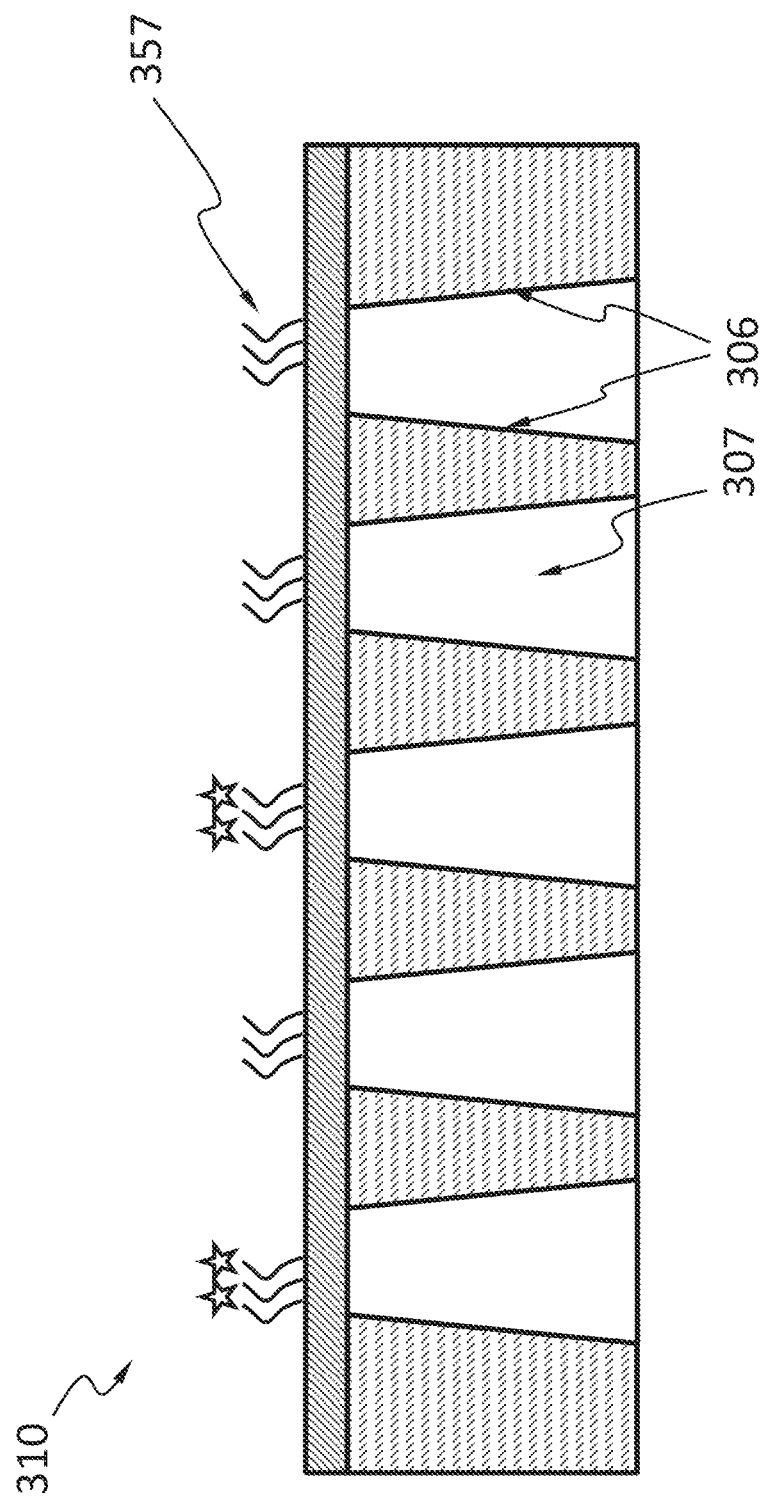
FIG. 3B schematically shows a probe carrier 310 wherein the sidewall of the hole is not perpendicular to the transparent window, according to an embodiment.

In the embodiments as shown in FIGS. 3A and 3B, the probes and the substrate are on opposite sides of the probe carrier. In embodiments as shown in FIGS. 4A and 4B, the probes and the substrate are deposited on the same side of the probe carrier.

Figure 4B:
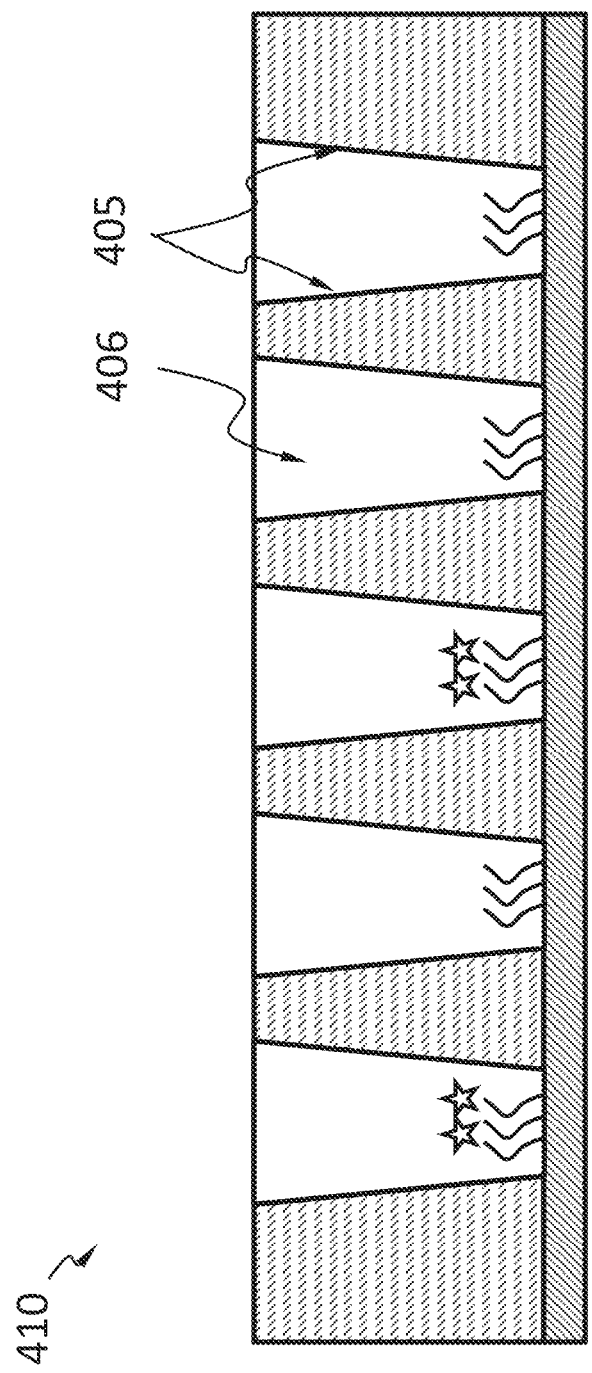
FIG. 4B schematically shows a probe carrier 410 wherein the sidewall of the hole is not perpendicular to the transparent window, according to an embodiment.

In the embodiments as shown in in FIGS. 3A and 4A, the sidewall 305 of the hole 302 or sidewall 405 of the hole 402 may be perpendicular to the transparent window. In the embodiments as shown in FIGS. 3B and 4B, the sidewall 306 of the hole 307 or the sidewall 406 of the hole 407 may be not perpendicular to the transparent window. The size and shape of sidewall of the holes may be controlled by a suitable wet or dry etching technique.

Figure 4C:
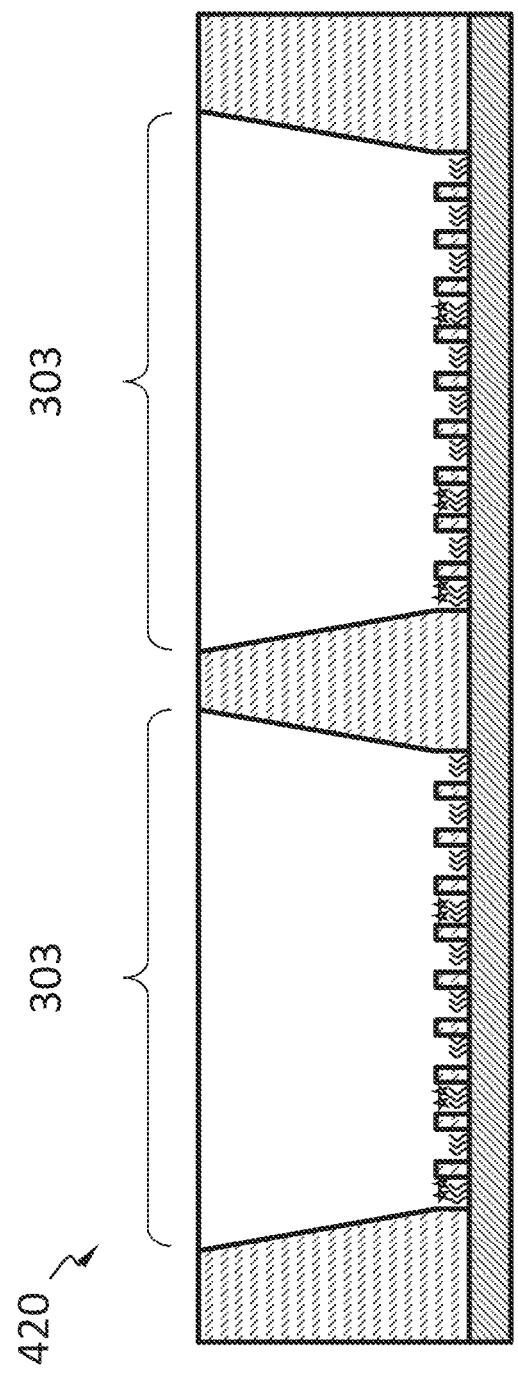
FIG. 4C schematically shows a probe carrier 420, according to an embodiment.

In an embodiment as shown in in FIG. 4C, multiple locations on a single transparent window 303 are configured to have probes attached thereto. The configuration of more than one location provides options of attaching different probes and enhancing the flexibility of the microarray.

Figure 5A:
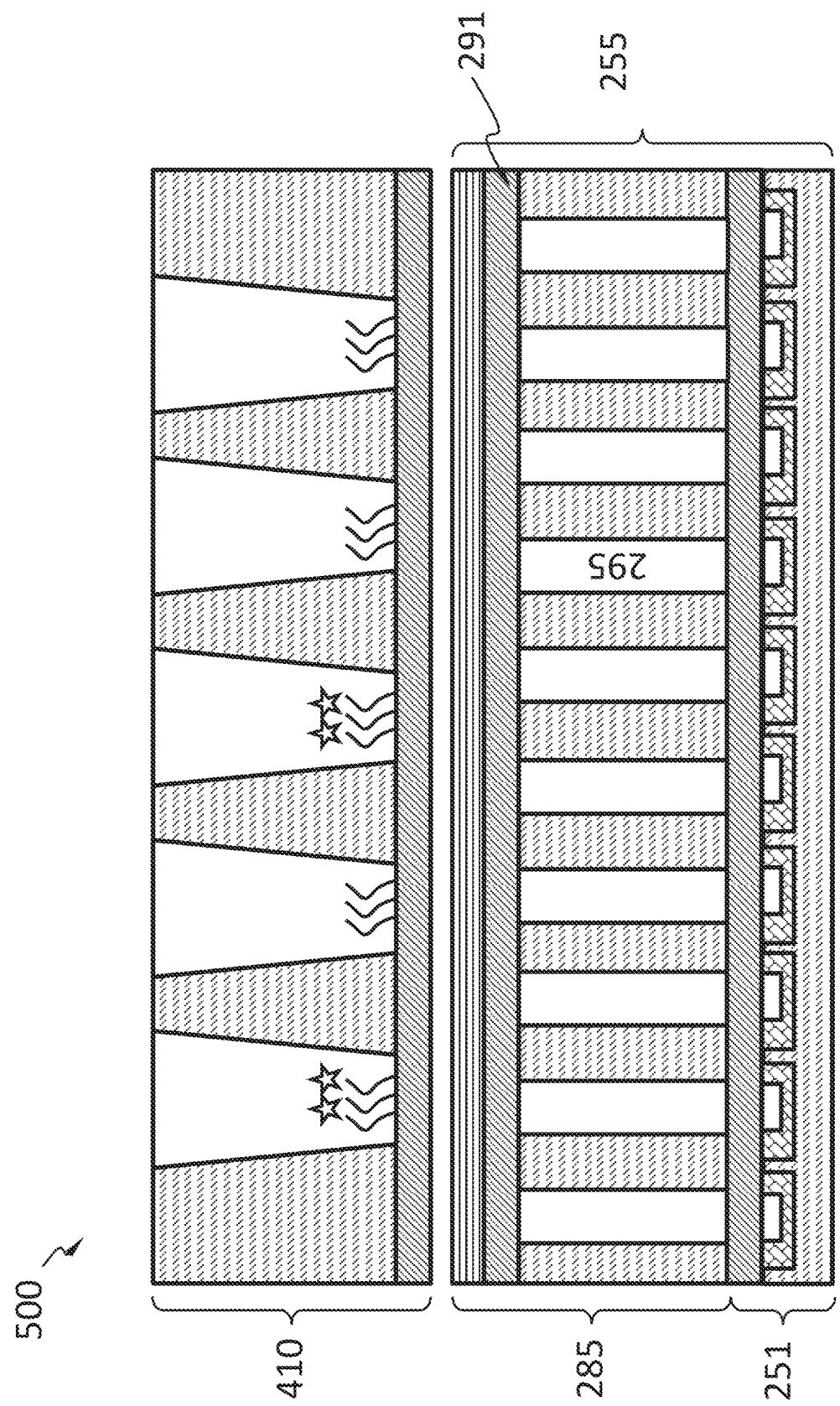
FIG. 5A schematically shows an apparatus 500 with a probe carrier 410, according to an embodiment.

In an embodiment as shown in FIG. 5A, an apparatus 500 comprises a probe carrier 410 and a microarray 255 that comprises an optical system 285 with collimators 295 and an integrated sensor 251. The probe carrier 410 may be mounted to the microarray 255 with a suitable technique. The biosensor function of the apparatus 500 may be carried out with appropriate probes on the probe carrier 410.

In an embodiment, the transmissive layer 291 may be an insulating material such as silicon oxide or silicon nitride. In an embodiment, the transmissive layer 291 may even be omitted.

Figure 5B:
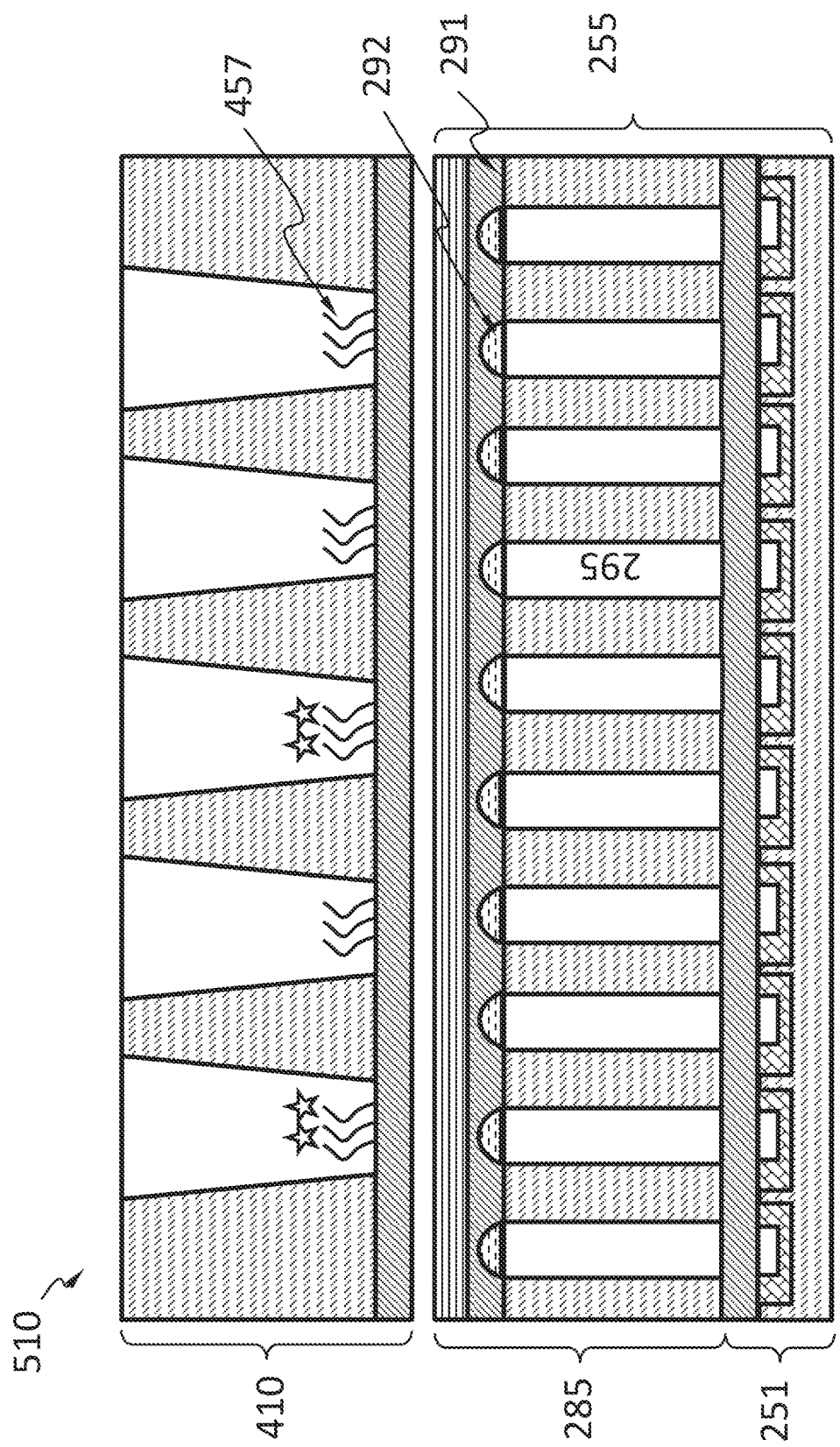
FIG. 5B schematically shows an apparatus 510 comprising microlens and a probe carrier 410, wherein the microlens may be fabricated in the passivation layer, according to an embodiment.
Figure 5C:
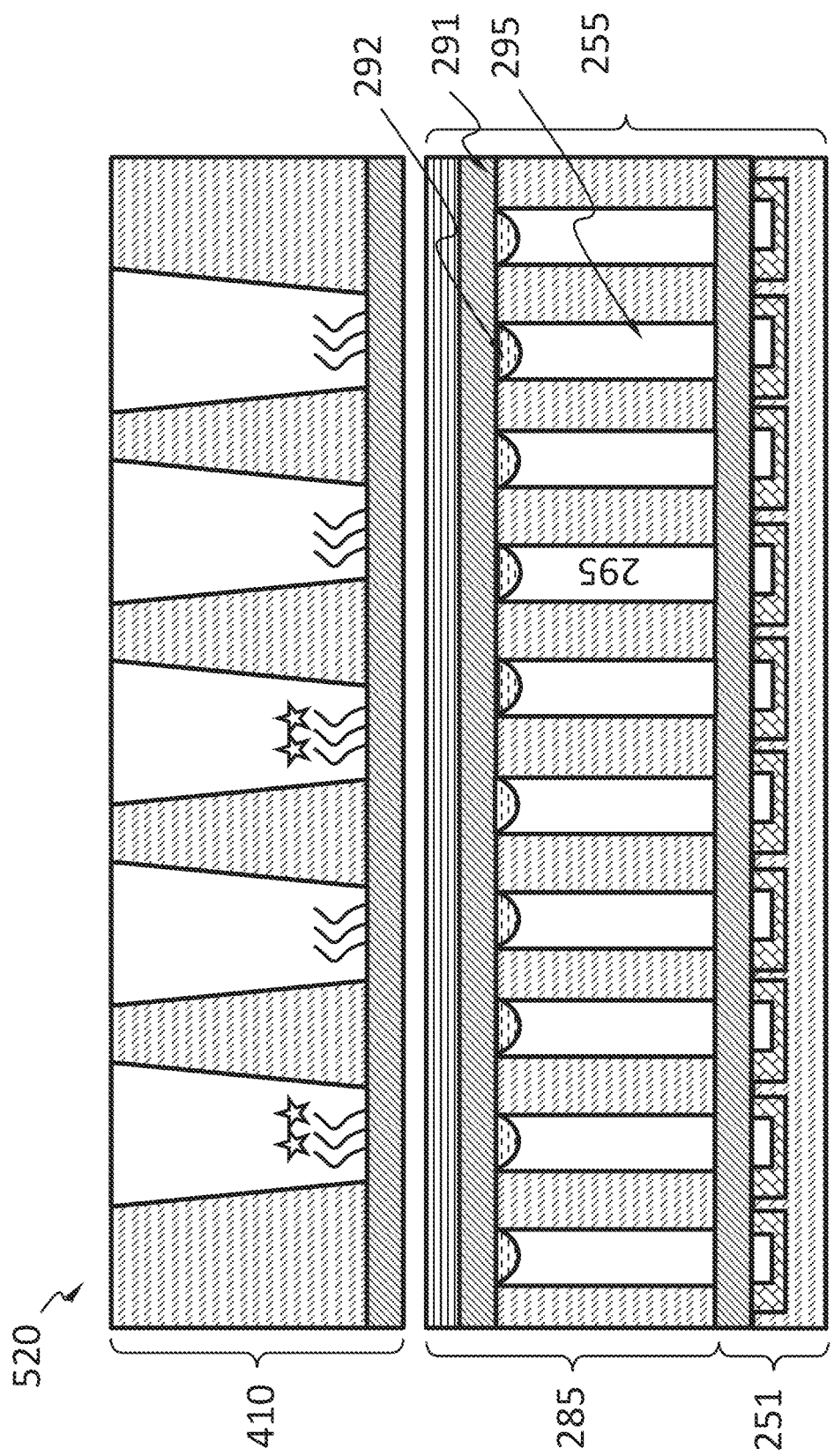
FIG. 5C schematically shows an apparatus 520 comprising microlens and a probe carrier 410, wherein the microlens may be fabricated in the collimators, according to an embodiment.

In an embodiment as shown in FIG. 5B, an apparatus 510 comprises a probe carrier 410 and a microarray 255 that comprises an optical system 285 with collimators 295 and an integrated sensor 251, wherein the optical system 285 may have a plurality of microlens 292. The microlens 292 may be fabricated in the passivation layer 291 as shown in FIG. 5B. Alternatively, the microlens 292 may be fabricated in the collimators 295 as shown in FIG. 5C. The microlens 292 may be configured to focus light generated by the probes into the collimators 295. The microlens 292 may be configured to direct a greater portion of luminescence signal from probes into the pixels coupled thereto. For example, a microlen 292 may capture the portion 273 that otherwise would not reach the pixel coupled to the location 256 where the portion 273 is from.

In embodiments as shown in FIG. 5A-5C, a transparent window of the probe carrier encompasses more than one of the collimators. This is achieved by controlled fabrication process such that the holes in the probe carrier have a greater width than the width of the collimators in the microarray. As used herein, the width of the hole or the width of the collimators refers to a size in the dimension that is parallel to the plane of the probe carrier. In such embodiments, no alignment of the probe carrier with the microarray is required during assembly of the probe carrier with the microarray to form the biosensor apparatus.

Figure 6A:
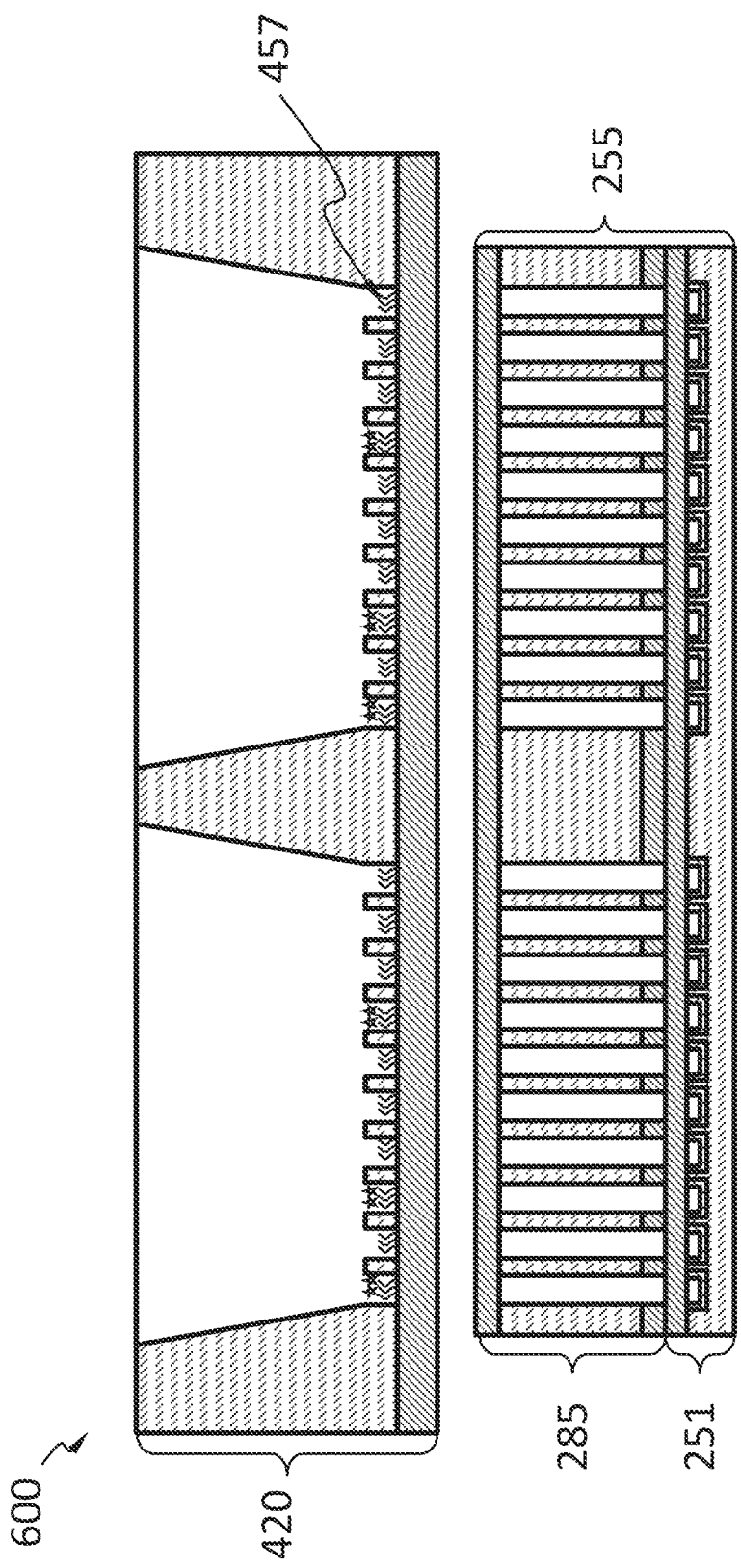
FIG. 6A schematically shows an apparatus 600 with a probe carrier 420, according to an embodiment.
Figure 6B:
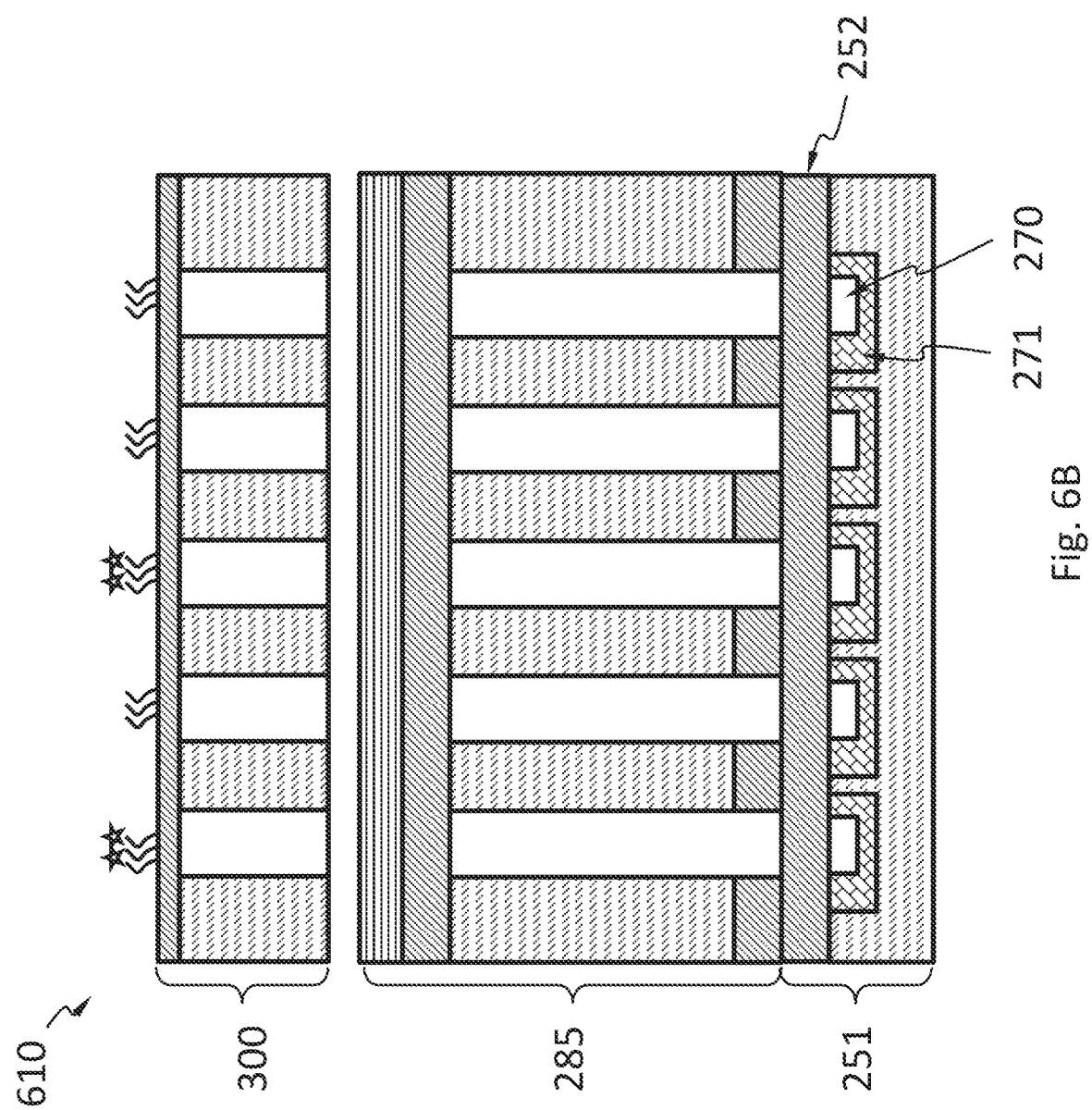
FIG. 6B schematically shows an apparatus 610 with a probe carrier 300, according to an embodiment.

In embodiments as shown in FIGS. 6A and 6B, each location is aligned with one of the collimators. This is achieved by controlled fabrication process such that the holes in the probe carrier has a same width than the width of the collimators in the microarray, and appropriate alignment of the probe carrier with the microarray is required during assembly of the probe carrier with the microarray to form the biosensor apparatus.

In an embodiment as shown in FIG. 6A, an apparatus 600 comprises a probe carrier 420 and a microarray 255 that comprises an optical system with collimators 295 and an integrated sensor 251. In other embodiments, other types of probe carrier, including but not limited to, 300, 310, 400 or 410 may be used alternatively to form the biosensor apparatus. For example, in an embodiment as shown in FIG. 6B, an apparatus 610 comprises a probe carrier 300 and a microarray 255 that comprises an optical system with collimators 295 and an integrated sensor 251.

In other embodiments, other types of microarrays may be used with any of the aforementioned probe carriers to form a biosensor apparatus. Some examples of such microarrays are illustrated as below.

In an embodiment, the filter 290, the transmissive layer 291 if present, the microlens 292 if present and the collimator 295 may be integrated on the same substrate.

In an embodiment, the collimator 295 may be configured to essentially prevent (e.g., prevent more than 90%, 99%, or 99.9% of) light from passing if the deviation of the propagation direction of the light from an optical axis of the collimator 295 is greater than a threshold (e.g., 20°, 10°, 5°, or 1°). A portion 272 of the signals 258 may propagate towards the pixel 270 optically coupled to that location 156 but another portion 273 may be scattered towards neighboring pixels ("optical cross-talk") and/or away from all pixels 270. The collimator 295 may be configured to essentially eliminate optical cross-talk by essentially preventing the portion 273 from passing through the collimator 295. Generating the signals 258 may need an excitation radiation 261 (e.g., laser, UV light, etc.). A portion 262 of the excitation radiation 261 may pass through the locations 256 unscattered. A portion 263 of the excitation radiation 261 may be scattered into other directions towards some of the pixels 270 or away from all pixels 270. The portion 262 may be blocked by the filter 290 from reaching the pixels 270. The filter 290 may be sensitive to incident directions and may not block the portion 263, despite portions 262 and 263 have the same wavelength. The collimators 295 may be configured to essentially prevent the excitation radiation from passing through irrespective of the propagation direction, or to essentially prevent the portion 263 scattered away from the propagation direction of the portion 261 from passing through.

In an embodiment, each of the collimators 295 extends from one of the locations 256 to the pixel 270 optically coupled to that one location.

In an embodiment, the collimator 295 may have a core 296 surrounded by a sidewall 297.

Figure 7B:
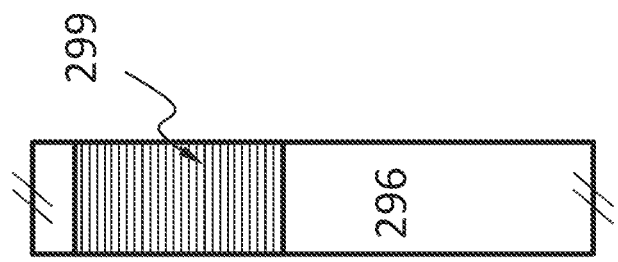
FIG. 7B schematically shows a collimator, according to an embodiment.
Figure 7A:
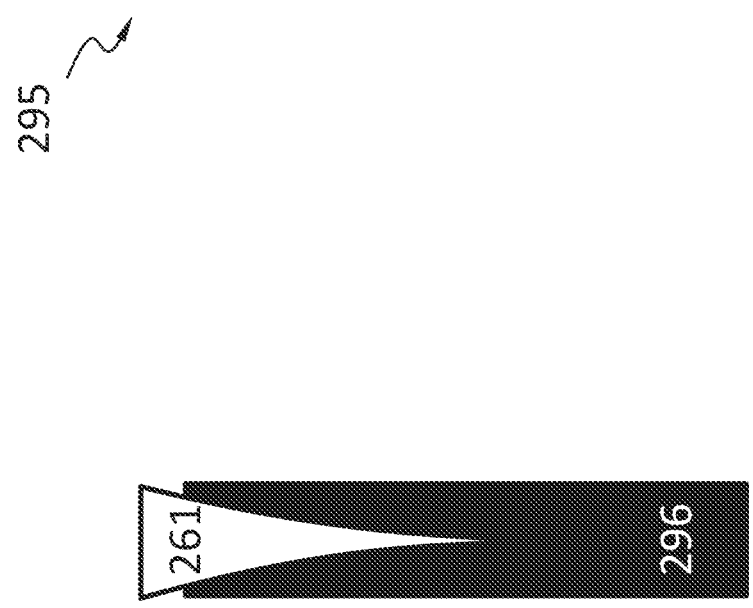
FIG. 7A schematically shows a collimator, according to an embodiment.

In an embodiment schematically shown in FIG. 7A, the core 296 may be a material that essentially prevents (e.g., prevents more than 90%, 99%, or 99.9% of) the excitation radiation 261 from passing through irrespective of the propagation direction of the excitation radiation 261. For example, the core 296 may be a material that attenuates (absorbs) the excitation radiation 261. The core 296 may allow the signals 258 to pass through essentially unabsorbed. In this embodiment, the filter 290 may be omitted.

In an embodiment schematically shown in FIG. 7B, the core 296 may have a structure 299 that essentially prevents (e.g., prevents more than 90%, 99%, or 99.9% of) a portion of the excitation radiation 261 from passing through if the deviation of the propagation direction of the portion (e.g., portion 272) from the optical axis of the collimator 295 is smaller than a threshold (e.g., 20°, 10°, 5°, or 1°). For example, the structure 299 may have a dichroic filter, a meta-material, quantum dots or a photonic crystal. The core 296 may allow the signals 258 to pass through essentially unabsorbed (i.e., less than 10% absorbed). In this embodiment, the filter 290 may be omitted.

In an embodiment, schematically shown in FIG. 7C, the sidewall 297 of the collimator 295 may attenuate (absorb) the excitation radiation. The portion 263 of the excitation radiation 261 may pass through the filter 290 and enter the collimator 295 but likely to reach the sidewall 297 before it can reach the pixels 270. The sidewall 297 that can attenuate (absorb) the excitation radiation will essentially prevent stray excitation radiation from reaching the pixels 270. In an embodiment, the core 296 may be a void space. Namely, the sidewall 297 surrounds a void space.

In an embodiment, the sidewall 297 may attenuate (absorb) any portion of the signal 258 reaching the sidewall, which will essentially prevent optical cross-talk.

In an embodiment, schematically shown in FIG. 7D, the sidewall 297 is textured. For example, the interface 298 between the sidewall 297 and the core 296 (which can be a void space) may be textured. Textured sidewall 297 can help further attenuate light incident thereon.

Figure 7E:
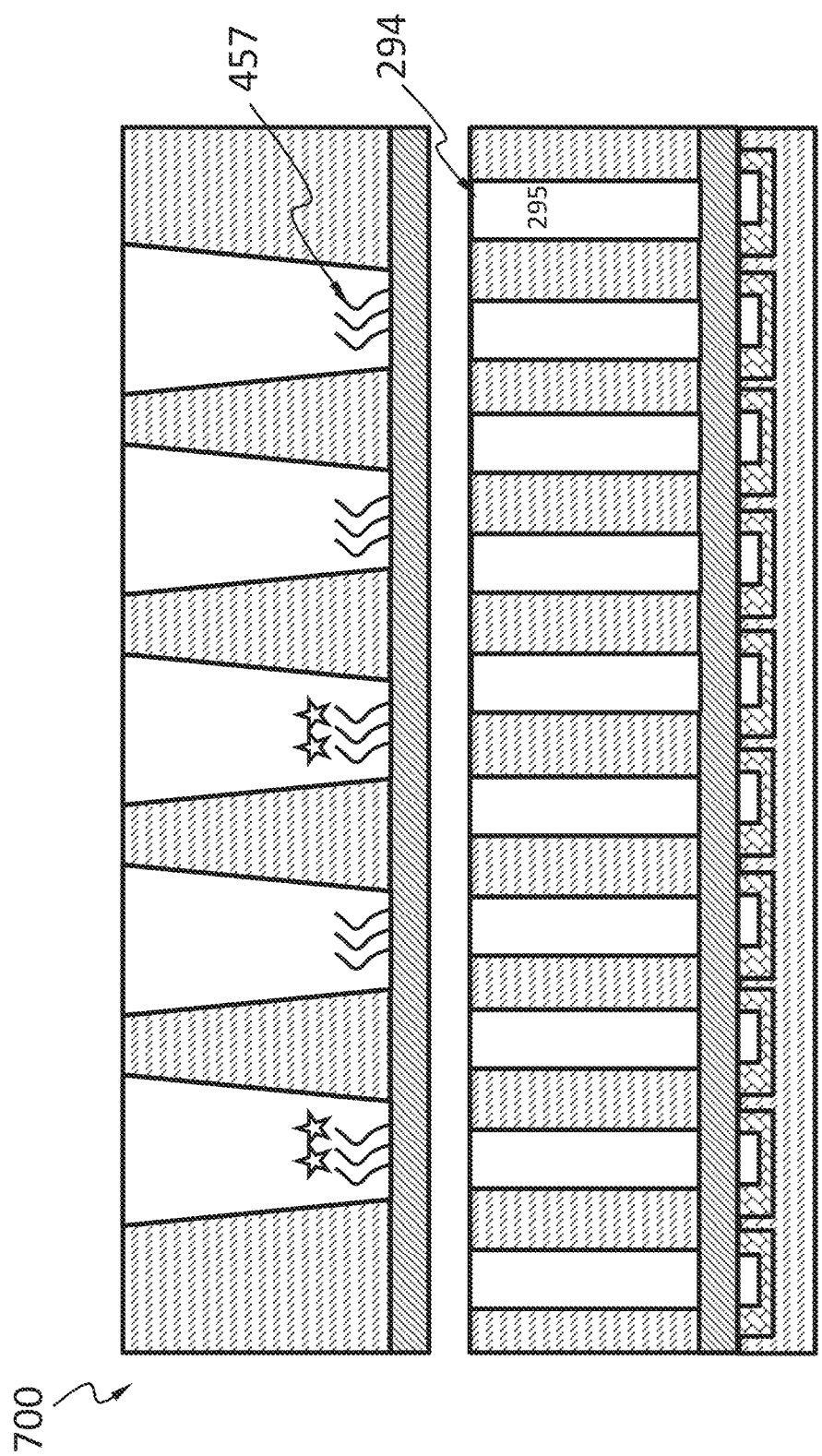
FIG. 7E schematically shows an apparatus 700 wherein the filter and the transmissive layer are both omitted, according to an embodiment.

In an embodiment, schematically shown in FIG. 7E, in apparatus 700, the filter 290 and the transmissive layer 291 may be both omitted. The collimator 295 may have a top surface 294 exposed. The top surface 294 may be of a different material from its neighboring surface, thereby facilitating functionalization of the top surface 294. The probes 457 may be selectively attached directly to the top surface 294.

Figure 7F:
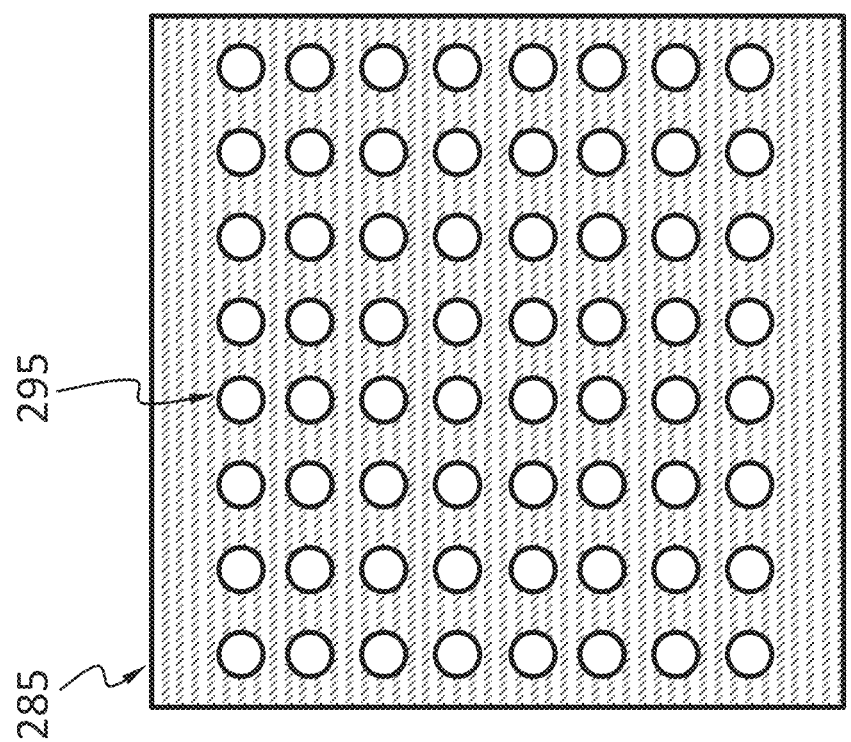
FIG. 7F and FIG. 7G each schematically show that the optical system may have a plurality of collimators arranged in an array, according to an embodiment.
Figure 7G:
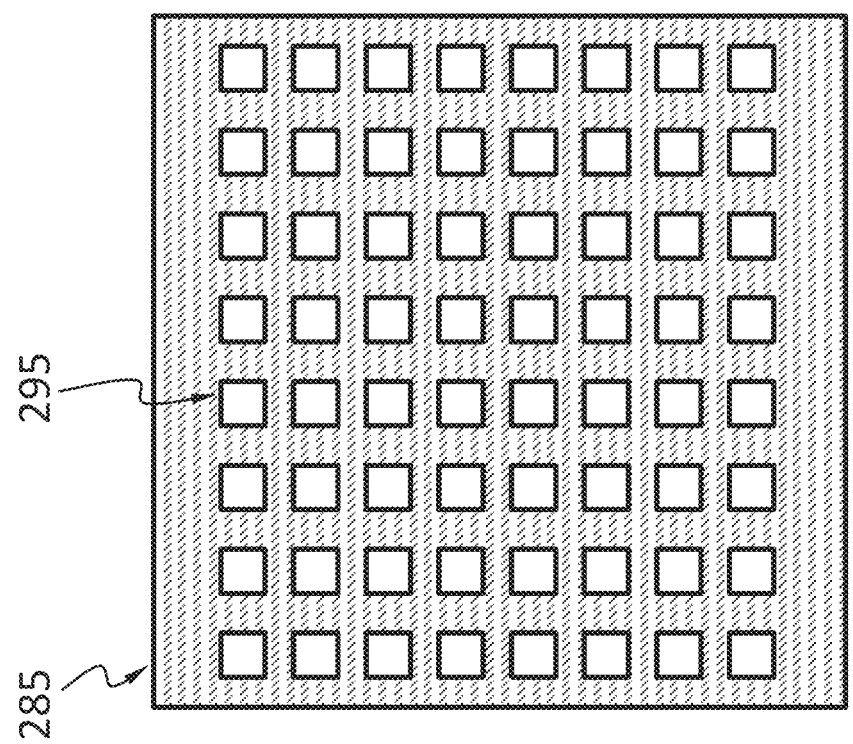

In an embodiment, schematically shown in FIG. 7F and FIG. 7G, the optical system 285 may have a plurality of collimators 295 arranged in an array. For example, the optical system 285 may have a dedicated collimator 295 for each pixel 270. For example, the optical system 285 may have a collimator 295 shared by a group of pixels 270. The collimator 295 may have any suitable cross-sectional shape, such as circular, rectangular, and polygonal.

In an embodiment, the collimators 295 may be made by etching (by e.g., deep reactive ion etching (deep RIE), laser drilling) holes into a substrate. The sidewall 297 may be made by depositing a material on the sidewall of the holes. The core 296 may be made by filling the holes. Planarization may also be used in the fabrication of the collimators 295.

In an embodiment, the filter 290 may be omitted or its function may be integrated into the collimators 295.

In an embodiment as schematically shown in FIG. 8, in apparatus 800, the optical system 285 may have a microfluidic system 850 to deliver reactants such as the analyte and reaction product to and from the locations 256. The microfluidic system 850 may have wells, reservoirs, channels, valves or other components. The microfluidic system 850 may also have heaters, coolers (e.g., Peltier devices), or temperature sensors. The heaters, coolers or temperature sensors may be located in the optical system 285, above or in the collimators 295. The heaters, coolers or temperature sensors may be located above or in the sensor 251. The biosensor apparatus 800 may be used for a variety of assays. For example, the biosensor apparatus 800 can be used to conduct real-time polymerase chain reaction (e.g., quantitative real-time PCR (qPCR)). Real-time polymerase chain reaction (real-time PCR) detects amplified DNA as the reaction progresses. This is in contrast to traditional PCR where the product of the reaction is detected at the end. One real-time PCR technique uses sequence-specific probes labelled with a fluorophore which fluoresces only after hybridization of the probe with its complementary sequence, which can be used to quantify messenger RNA (mRNA) and non-coding RNA in cells or tissues.

The optical system 285 and the sensor 251 may be fabricated in separate substrates and bonded together using a suitable technique, such as, flip-chip bonding, wafer-to-wafer direct bonding, or gluing.

Figure 9A:
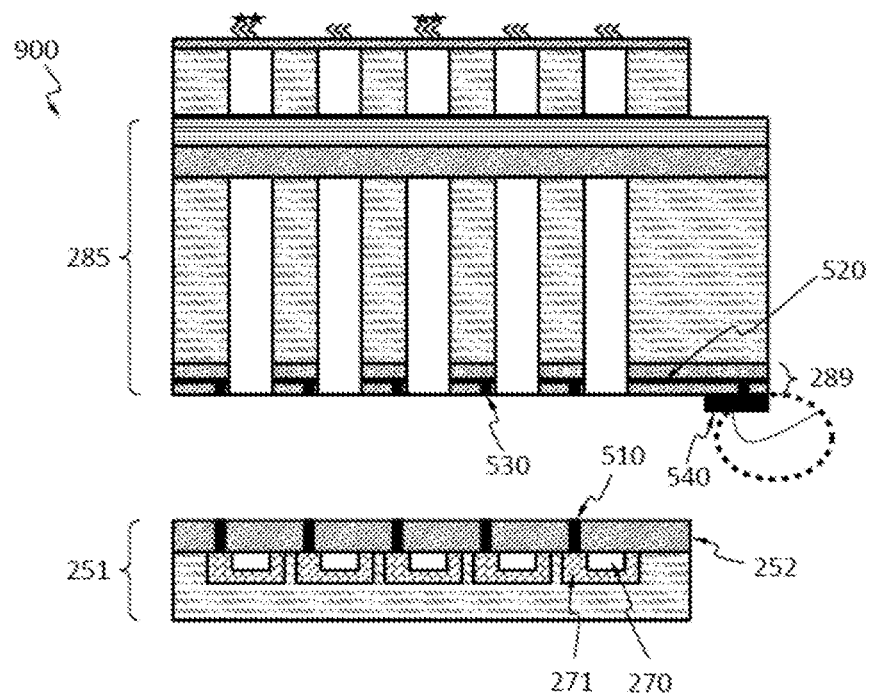
FIG. 9A schematically shows an apparatus 900 wherein a sensor in a microarray may have a signal transfer layer and that the optical system in the microarray may have a redistribution layer, according to an embodiment.

In an embodiment, schematically shown in FIG. 9A, in apparatus 900, the sensor 251 has a signal transfer layer 252. The signal transfer layer 252 may have a plurality of vias 510. The signal transfer layer 252 may have electrically insulation materials (e.g., silicon oxide) around the vias 510. The optical system 285 may have a redistribution layer 289 with transmission lines 520 and vias 530. The transmission lines 520 connect the vias 530 to bonding pads 540. When the sensor 251 and the optical system 285 are bonded, the vias 510 and the vias 530 are electrically connected. This configuration shown in FIG. 9A allows the bonding pads 540 to be positioned away from the probes 257.

Figure 9B:
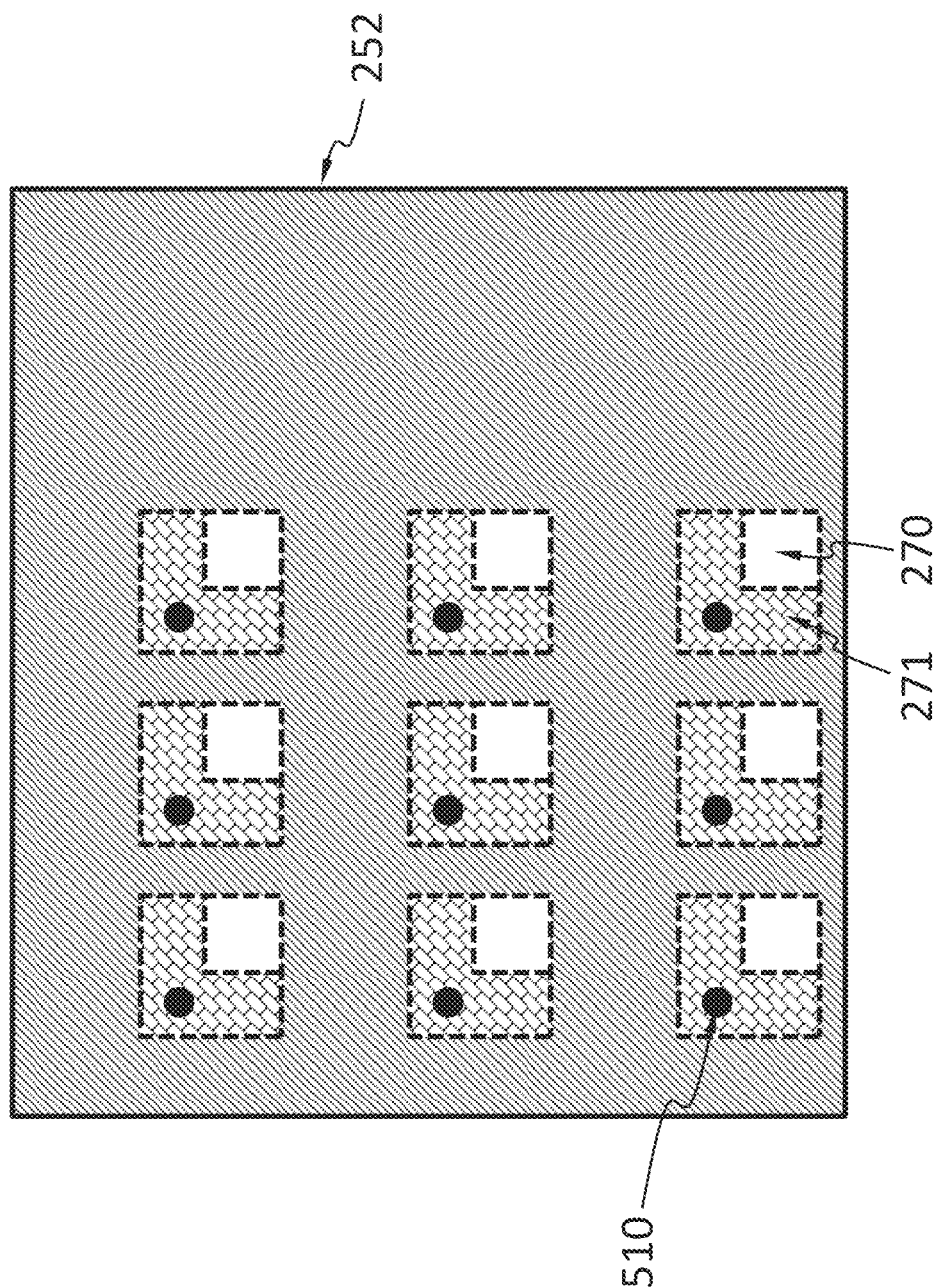
FIG. 9B schematically shows a top view of the sensor in FIG. 9A.
Figure 9C:
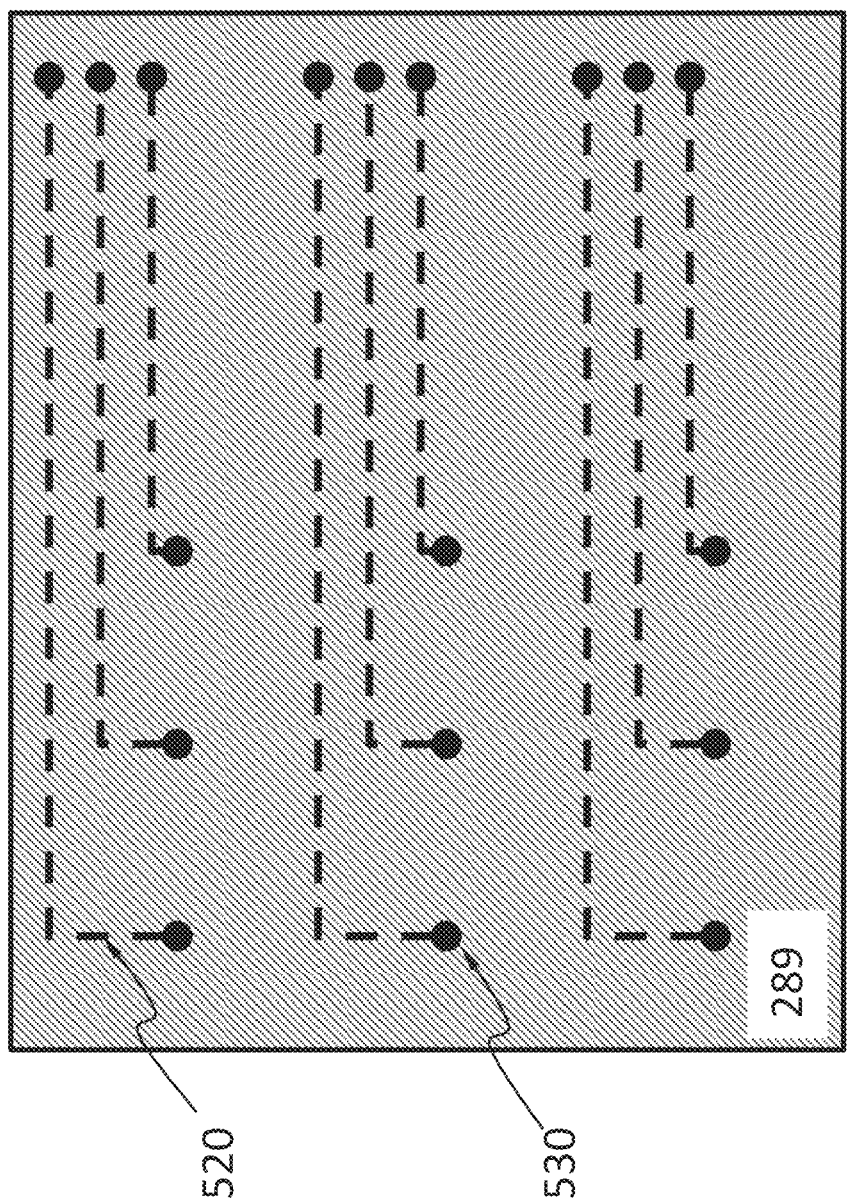
FIG. 9C schematically shows a bottom view of the optical system in FIG. 9A.

FIG. 9B shows a top view of the sensor 251 in FIG. 9A to illustrate the positions of the vias 510 relative to the pixels 270 and the control circuit 271. The pixels 270 and the control circuit 271 are shown in dotted lines because they are not directly visible in this view. FIG. 9C shows a bottom view of the optical system 285 in FIG. 9A to illustrate the positions of the vias 530 relative to the transmission lines 520 (shown as dotted lines because they are not directly visible in this view).

Figure 10A:
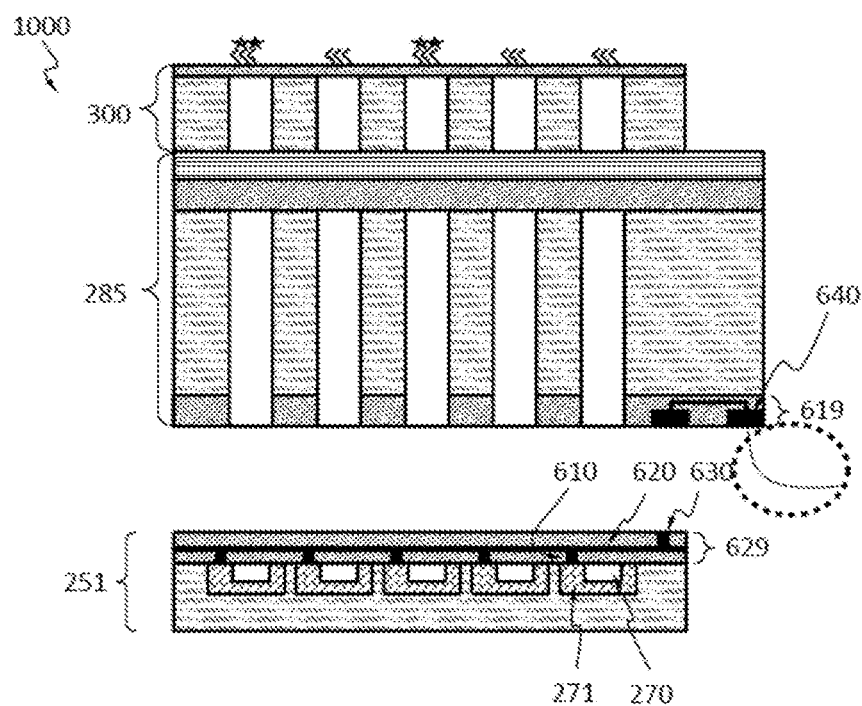
FIG. 10A schematically shows an apparatus 1000 wherein a sensor in a microarray may have a redistribution layer and that the optical system in the microarray may have a signal transfer layer, according to an embodiment.

In an embodiment, schematically shown in FIG. 10A, in apparatus 1000, the sensor 251 has a redistribution layer 629. The redistribution layer 629 may have a plurality of vias 610 and a plurality of transmission lines 620. The redistribution layer 629 may have electrically insulation materials (e.g., silicon oxide) around the vias 610 and the transmission lines 620. The vias 610 electrically connect the control circuit 271 to the transmission lines 620. The optical system 285 may have a layer 619 with bonding pads 640. The redistribution layer 629 may also have vias 630 electrically connecting the transmission lines 620 to the bonding pads 640, when the sensor 251 and the optical system 285 are bonded. The bonding pads 640 may have two parts connected by a wire buried in the layer 619. This configuration shown in FIG. 10A allows the bonding pads 640 to be positioned on an opposite side from the probe carrier.

Figure 10B:
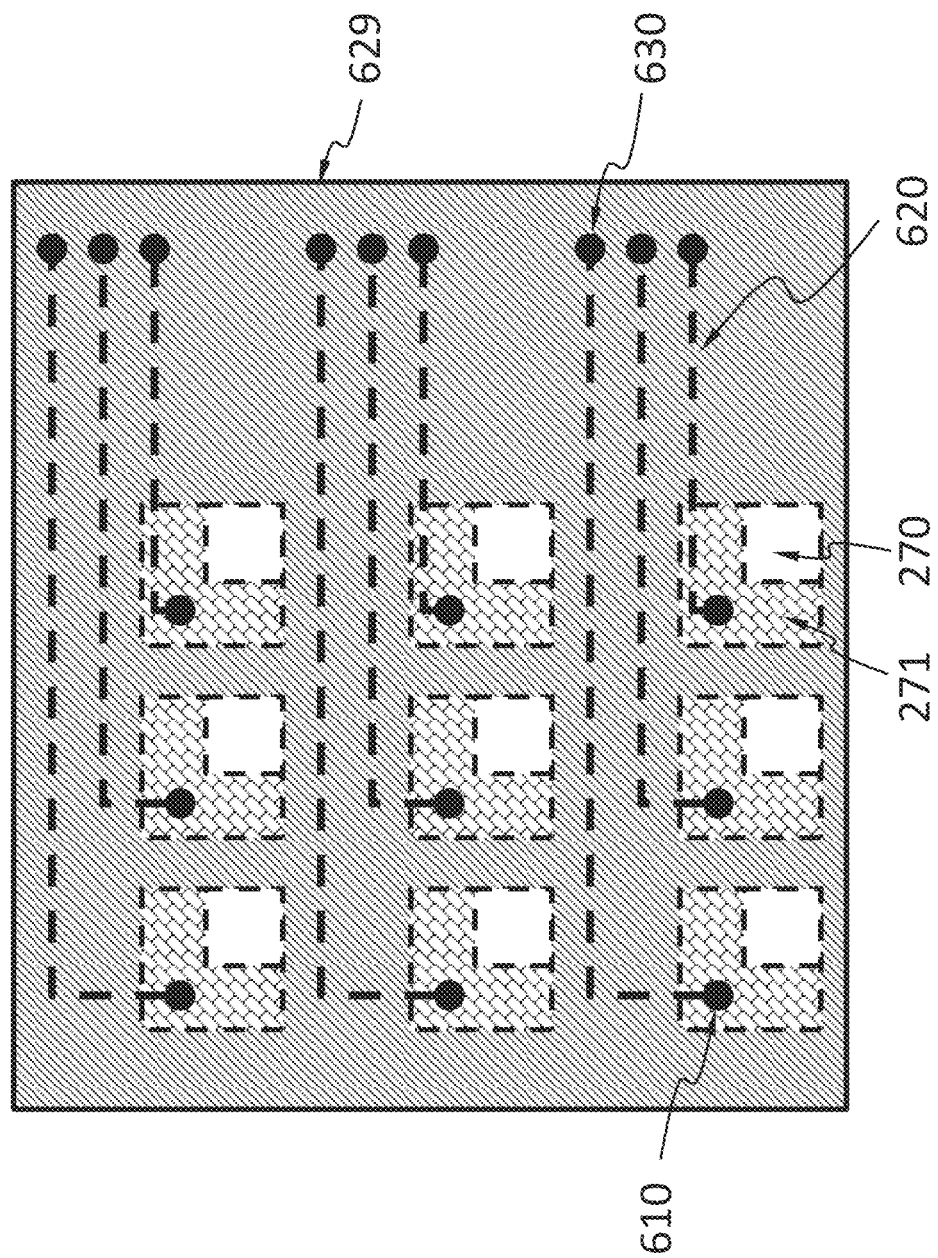
FIG. 10B schematically shows a top view of the sensor in FIG. 10A, according to an embodiment.
Figure 10C:
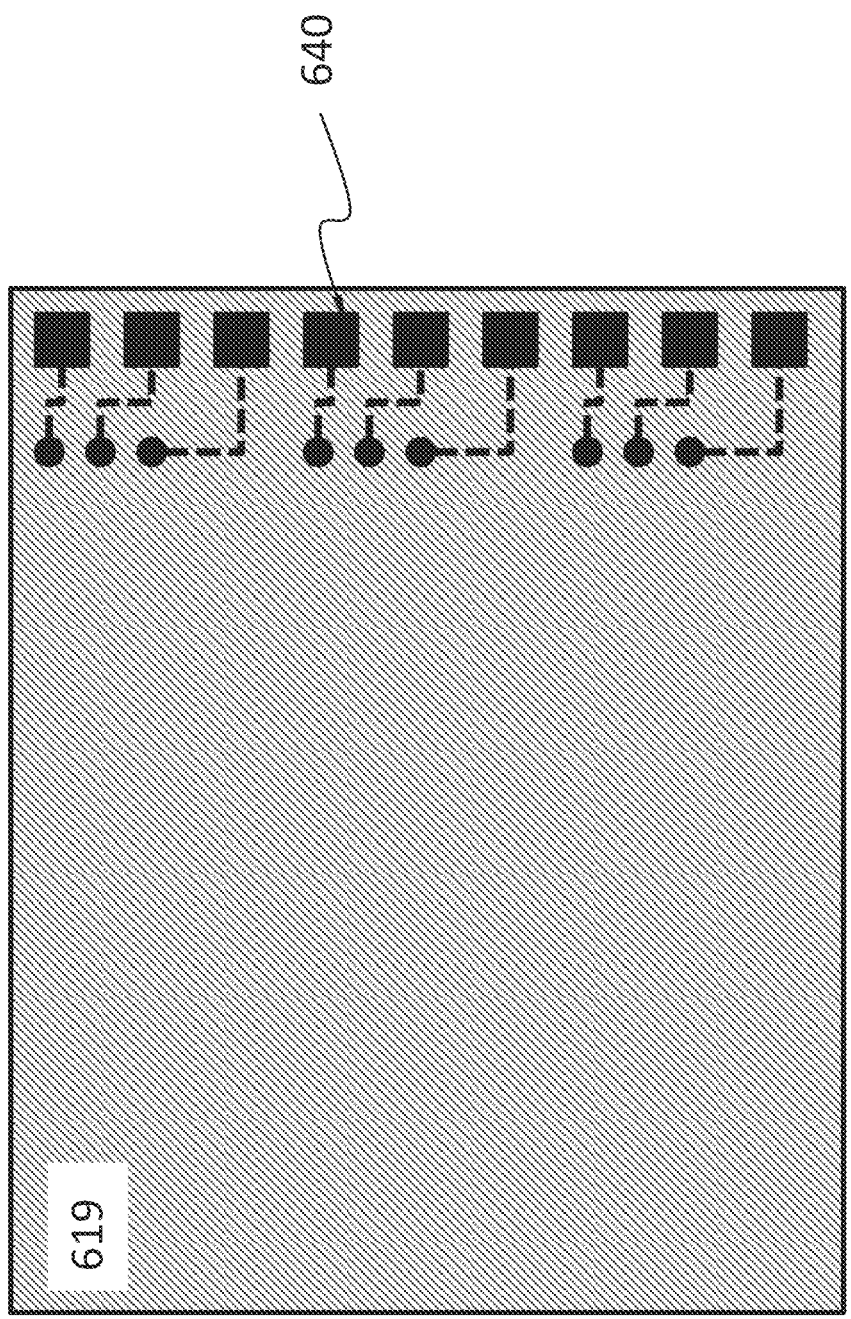
FIG. 10C schematically shows a bottom view of the optical system in FIG. 10A, according to an embodiment.

FIG. 10B shows a top view of the sensor 251 in FIG. 10A to illustrate the positions of the vias 610, the vias 630 and the transmission lines 620, relative to the pixels 270 and the control circuit 271, according to an embodiment. The pixels 270, the control circuit 271 and the transmission lines 620 are shown in dotted lines because they are not directly visible in this view. FIG. 10C shows a bottom view of the optical system 285 in FIG. 10A to illustrate the positions of the bonding pads 640, which are positioned to connect to the vias 630 shown in FIG. 10B. The bonding pads 640 may have two parts connected by a wire buried in the layer 619.

Figure 10D:
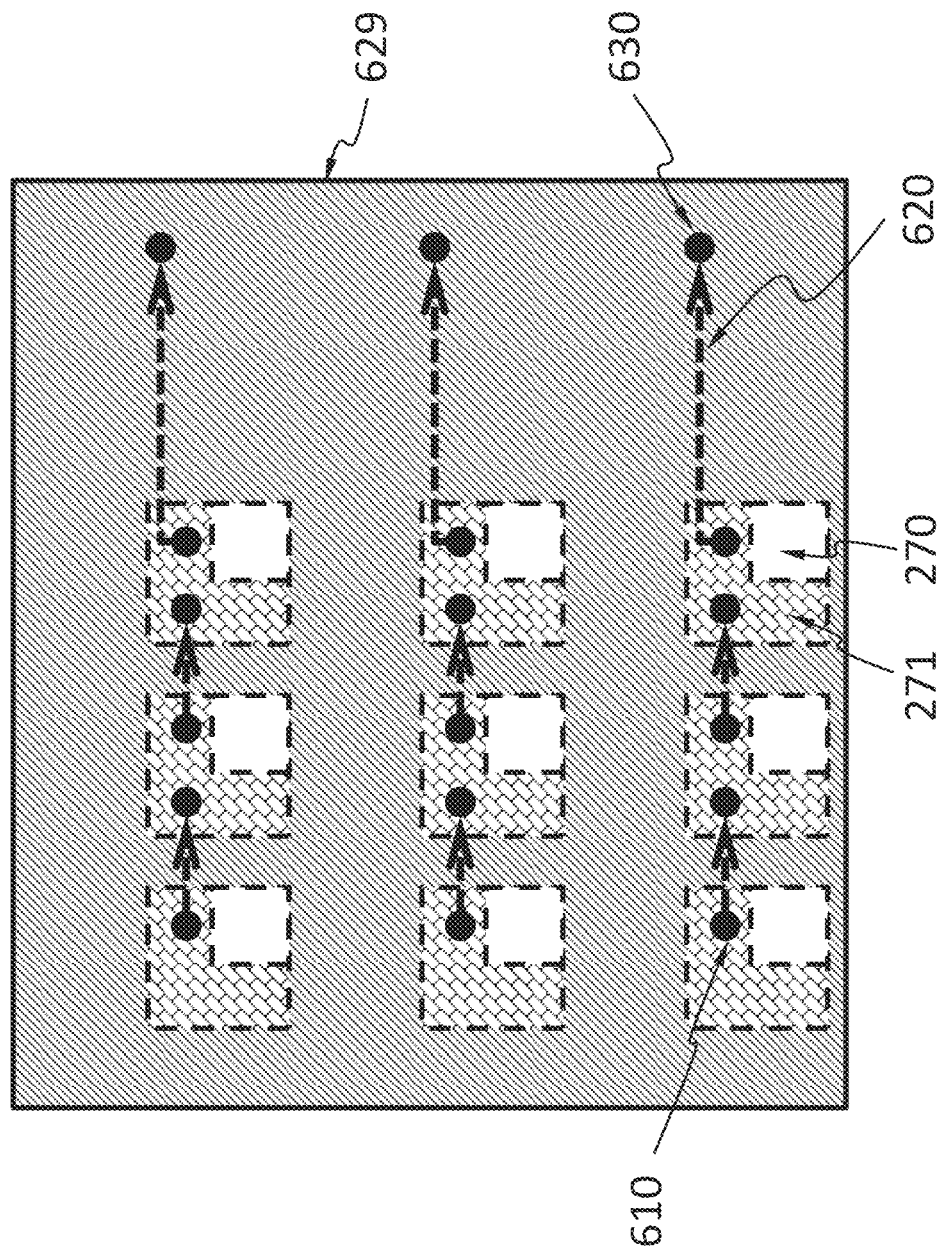
FIG. 10D schematically shows a top view of the sensor in FIG. 10A, according to an embodiment.
Figure 10E:
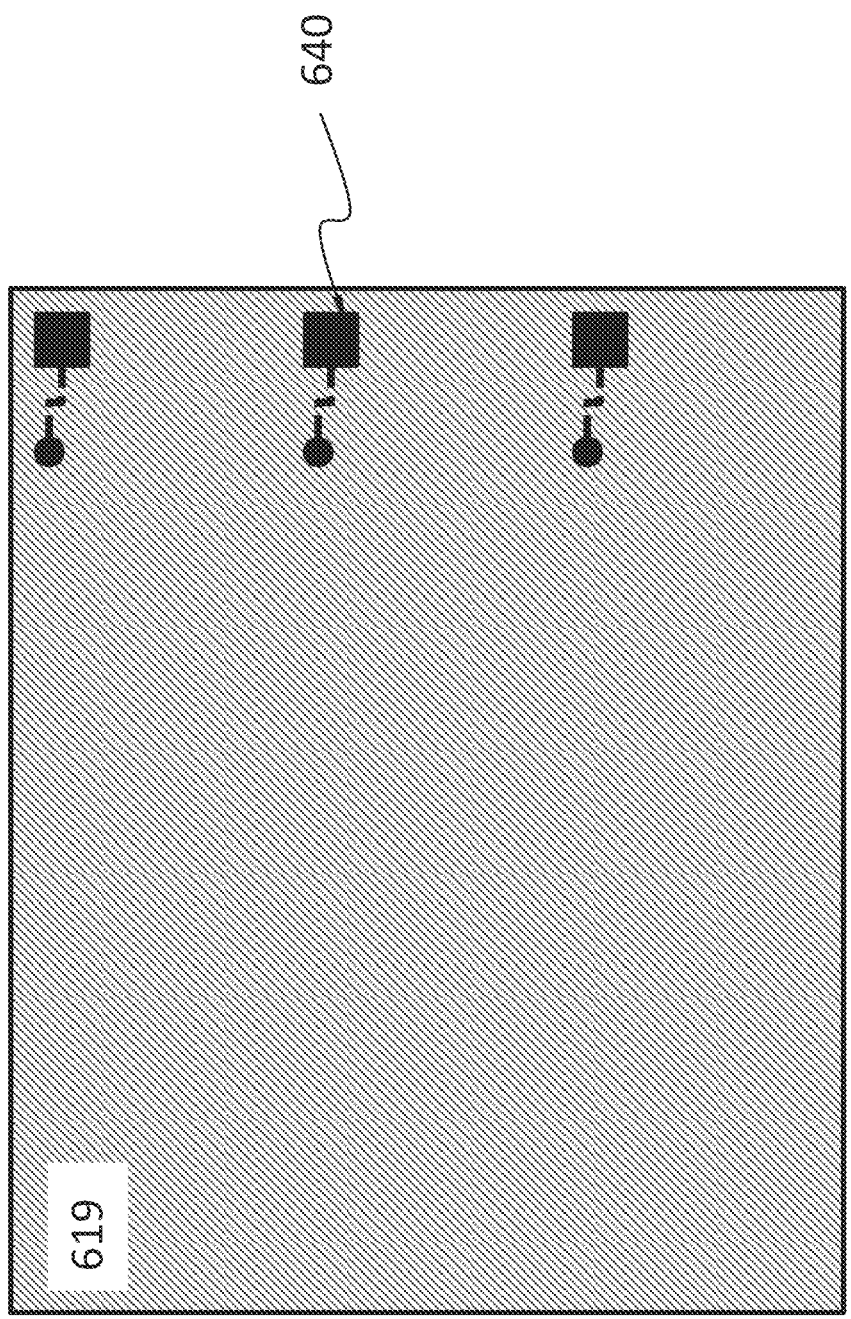
FIG. 10E schematically shows a bottom view of the optical system in FIG. 10A to illustrate the positions of the bonding pads, which are positioned to connect to the vias shown in FIG. 10D.

FIG. 10D shows a top view of the sensor 251 in FIG. 10A to illustrate the positions of the vias 610, the vias 630 and the transmission lines 620, relative to the pixels 270 and the control circuit 271, according to an embodiment. The pixels 270, the control circuit 271 and the transmission lines 620 are shown in dotted lines because they are not directly visible in this view. The pixels 270 may be read out column by column. For example, signal from one 270 may be stored in register in the control circuit 271 associated with that pixel 270; the signal may be successively shifted from one column to the next, and eventually to other processing circuitry through vias 630. FIG. 10E shows a bottom view of the optical system 285 in FIG. 10A to illustrate the positions of the bonding pads 640, which are positioned to connect to the vias 630 shown in FIG. 10D. The bonding pads 640 may have two parts connected by a wire buried in the layer 619.

Figure 10F:
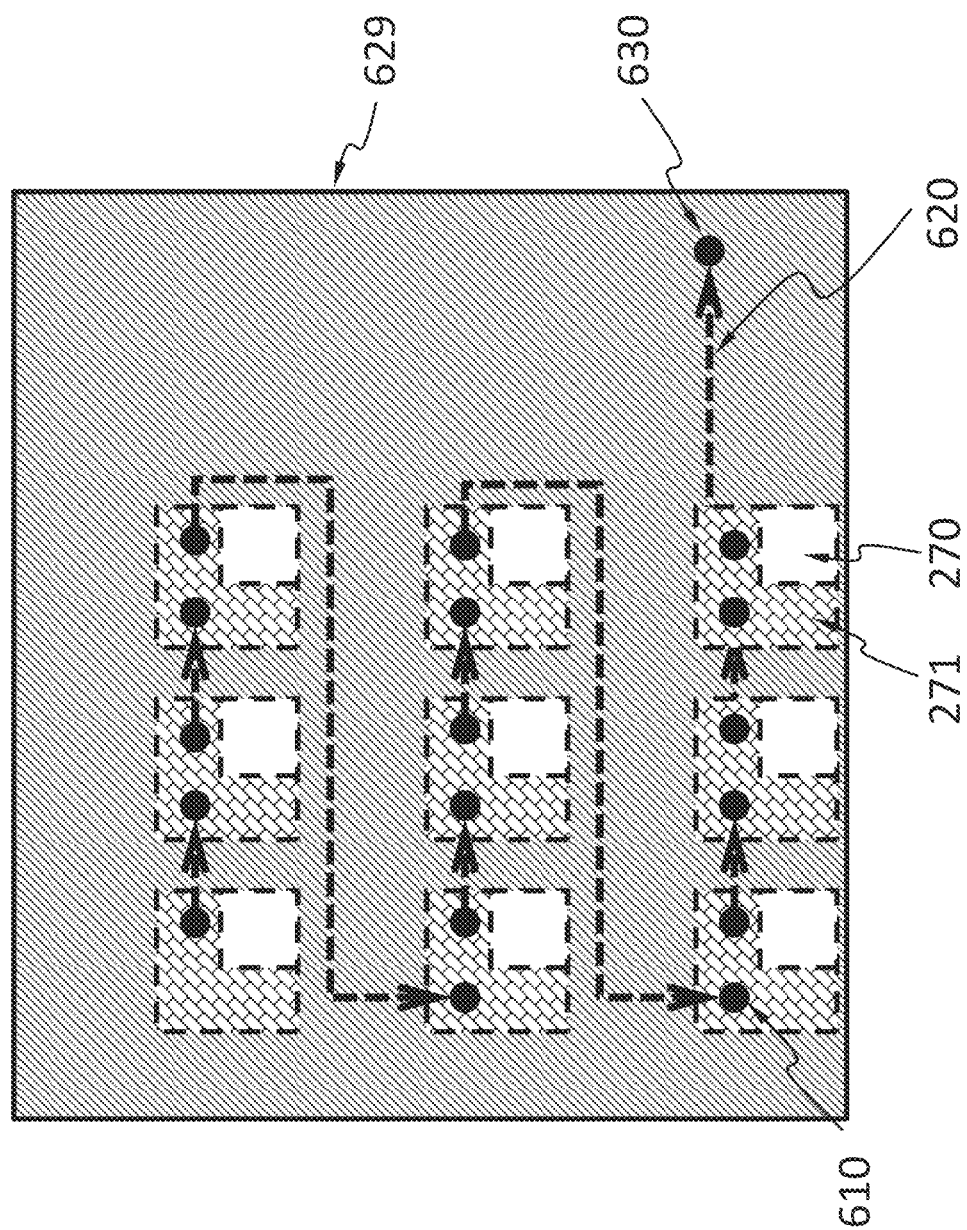
FIG. 10F schematically shows a top view of the sensor in FIG. 10A, according to an embodiment.
Figure 10G:
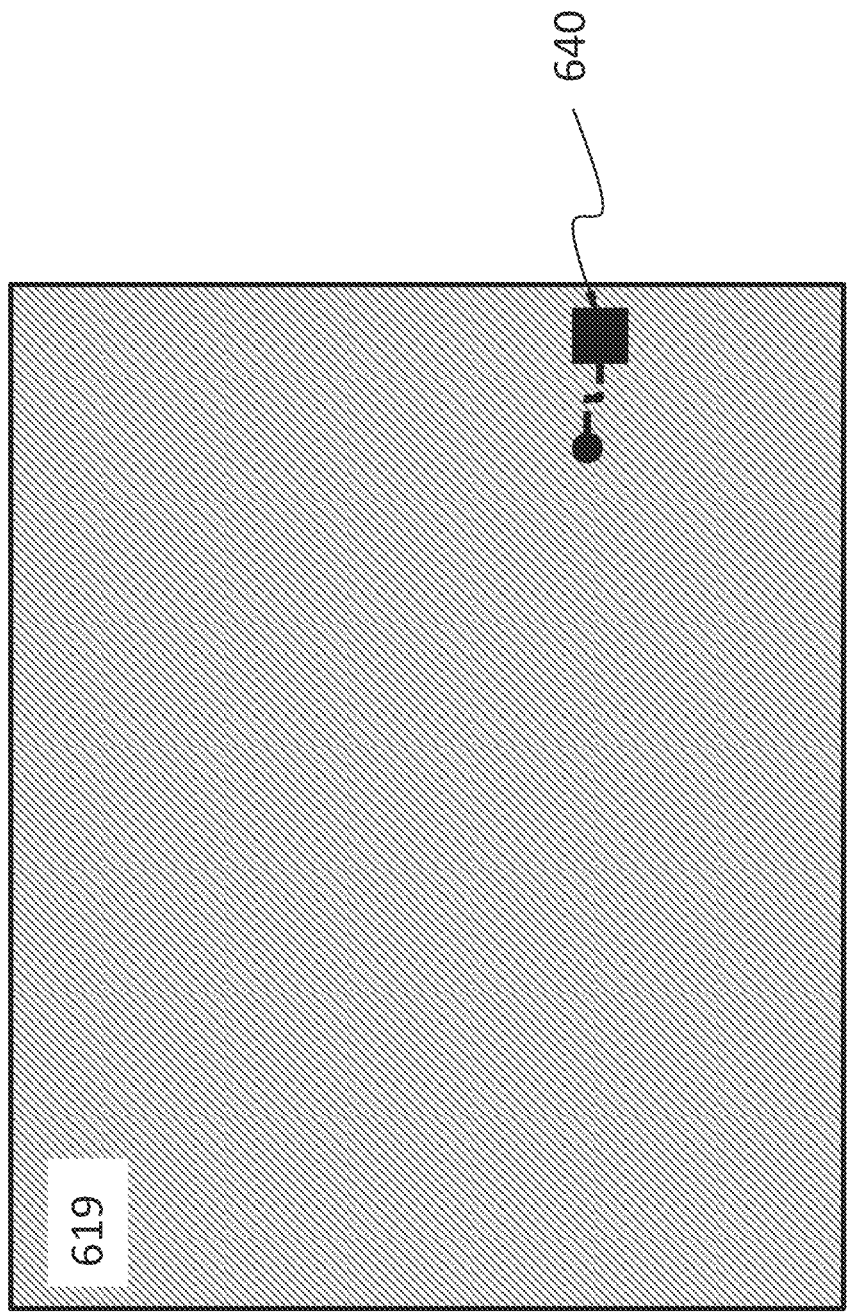
FIG. 10G schematically shows a bottom view of the optical system in FIG. 10A to illustrate the positions of the bonding pad, which are positioned to connect to the via shown in FIG. 10F.

FIG. 10F shows a top view of the sensor 251 in FIG. 10A to illustrate the positions of the vias 610, the via 630 and the transmission lines 620, relative to the pixels 270 and the control circuit 271, according to an embodiment. The pixels 270, the control circuit 271 and the transmission lines 620 are shown in dotted lines because they are not directly visible in this view. The pixels 270 may be read out pixel by pixel. For example, signal from one 270 may be stored in register in the control circuit 271 associated with that pixel 270; the signal may be successively shifted from one pixel to the next, and eventually to other processing circuitry through via 630. FIG. 10G shows a bottom view of the optical system 285 in FIG. 10A to illustrate the positions of the bonding pad 640, which are positioned to connect to the via 630 shown in FIG. 10F. The bonding pads 640 may have two parts connected by a wire buried in the layer 619.

Figure 11:
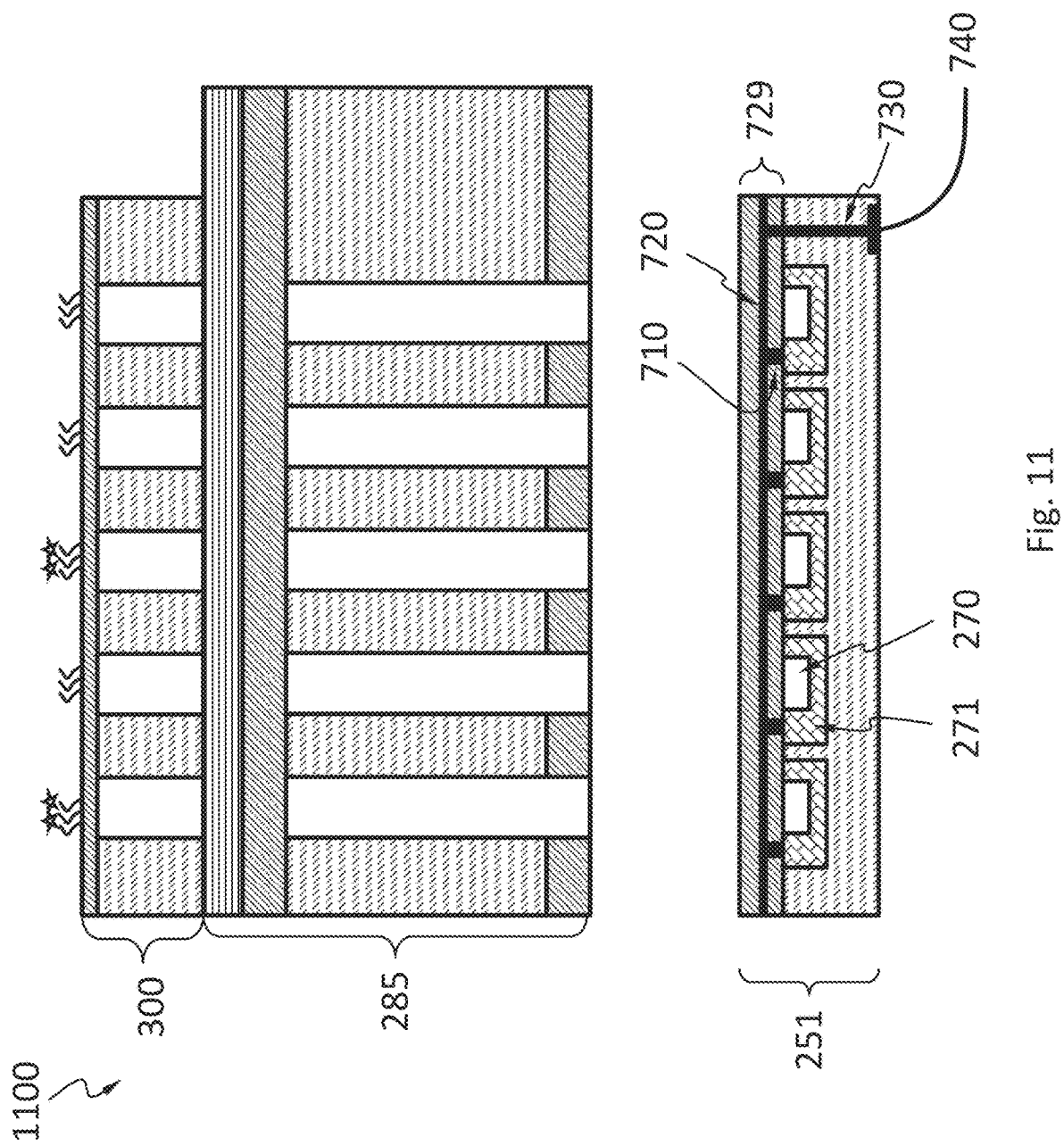
FIG. 11 schematically shows that system 1100 wherein a sensor in a microarray may have a redistribution layer with vias such as through-silicon vias (TSV) configured to electrically connect the transmission lines in the redistribution layer to bonding pads on the side opposite from the redistribution layer, according to an embodiment.

In an embodiment, schematically shown in FIG. 11, in apparatus 1100, the sensor 251 has a redistribution layer 729. The redistribution layer 729 may have a plurality of vias 710 and a plurality of transmission lines 720. The redistribution layer 729 may have electrically insulation materials (e.g., silicon oxide) around the vias 710 and the transmission lines 720. The vias 710 electrically connect the control circuit 271 to the transmission lines 720. The redistribution layer 729 may also have vias 730 (e.g., through-silicon vias (TSV)) electrically connecting the transmission lines 720 to bonding pads 740 on the side opposite from the redistribution layer 729. This configuration shown in FIG. 11 allows the bonding pads 740 to be positioned on an opposite side from the probe carrier.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An apparatus comprising:
    a probe carrier comprising:
        a first substrate comprising a first plurality of through holes in the first substrate,
        a transparent window attached to the first substrate and across an opening of each of the first plurality of through holes, wherein the transparent window closes the opening; and
        probes attached to one or more locations on the transparent window, wherein interaction between the probes and an analyte generates a signal;
    a second substrate comprising a second plurality of through holes in the second substrate, wherein the second plurality of through holes are configured as a plurality of collimators;
    a sensor comprising a plurality of pixels configured to detect the signal;
    wherein the collimators are configured to essentially prevent light from passing if a deviation of a propagation direction of the light from an optical axis of the collimators is greater than a threshold.

2. The apparatus of claim 1, wherein the first substrate comprises silicon.

3. The apparatus of claim 1, wherein the probes and the first substrate are on a same side of the probe carrier.

4. The apparatus of claim 1, wherein the probes and the first substrate are on opposite sides of the probe carrier.

5. The apparatus of claim 1, wherein the transparent window is aligned with one of the collimators.

6. The apparatus of claim 1, wherein the transparent window encompasses more than one of the collimators.

7. The apparatus of claim 1, wherein the transparent window is a portion of a continuous transparent layer across the first substrate.

8. The apparatus of claim 1, wherein the transparent window has a thickness from 10 to 50 micrometers.

9. The apparatus of claim 1, wherein sidewalls of the first plurality of through holes are not perpendicular to the transparent window.

10. The apparatus of claim 1, wherein the sensor comprises a control circuit configured to control, acquire data from, or process data from the pixels.

11. The apparatus of claim 1, wherein the pixels are arranged such that each of the pixels is optically coupled to one or more of the locations.

12. The apparatus of claim 1, wherein the pixels are optically coupled to the locations by the collimators.

13. The apparatus of claim 1, wherein the signal is luminescence.

14. The apparatus of claim 1, wherein the optical system further comprises era transmissive layer.

15. The apparatus of claim 1, wherein the optical system further comprises a plurality of microlens.

16. The apparatus of claim 1, wherein the collimators comprise a meta-material, quantum dots or a photonic crystal.

17. The apparatus of claim 1, wherein the collimators are configured to eliminate optical cross-talk between neighboring pixels among the plurality of pixels.

18. The apparatus of claim 1, wherein sidewalls of the second plurality of through holes attenuate a portion of the signal reaching the sidewalls.

19. The apparatus of claim 1, wherein sidewalls of the second plurality of through holes are textured.

20. The apparatus of claim 1, wherein the optical system further comprises a filter, wherein the filter comprises a meta-material, quantum dots or a photonic crystal.

21. The apparatus of claim 1, wherein the pixels are arranged in an array and are configured to be read out column by column.

22. The apparatus of claim 1, wherein the pixels are arranged in an array and are configured to be read out pixel by pixel.

* * * * *